United States Patent
Ito et al.

(10) Patent No.: US 9,062,246 B2
(45) Date of Patent: Jun. 23, 2015

(54) FLUORESCENT COMPOUND, MAKING METHOD, AND FLUORESCENT RESIN COMPOSITION

(71) Applicant: Shin-Etsu Chemical Co., Ltd., Tokyo (JP)

(72) Inventors: Yusuke Ito, Joetsu (JP); Ayumu Kiyomori, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 179 days.

(21) Appl. No.: 13/761,191

(22) Filed: Feb. 7, 2013

(65) Prior Publication Data

US 2013/0207041 A1    Aug. 15, 2013

(30) Foreign Application Priority Data

Feb. 10, 2012 (JP) ................................ 2012-027589

(51) Int. Cl.

| | | |
|---|---|---|
| *C09K 11/06* | (2006.01) | |
| *C07F 7/18* | (2006.01) | |
| *H01L 51/00* | (2006.01) | |
| *H05B 33/14* | (2006.01) | |
| *H01L 51/50* | (2006.01) | |

(52) U.S. Cl.
CPC ............ *C09K 11/06* (2013.01); *H01L 51/0052* (2013.01); *H05B 33/14* (2013.01); *C09K 2211/1011* (2013.01); *C09K 2211/1014* (2013.01); *C07F 7/1864* (2013.01); *H01L 51/0054* (2013.01); *H01L 51/0058* (2013.01); *H01L 51/0094* (2013.01); *H01L 51/5012* (2013.01)

(58) Field of Classification Search
CPC .................. C07F 7/1864; C09K 11/06; C09K 2211/1011; C09K 2211/1014; H01L 51/0052; H01L 51/0054; H01L 51/0058; H01L 51/0094; H01L 51/5012
USPC .............................. 556/454, 456; 252/301.35
See application file for complete search history.

(56) References Cited

U.S. PATENT DOCUMENTS

| | | |
|---|---|---|
| 4,978,731 A | 12/1990 | Melancon et al. |
| 7,683,225 B2 | 3/2010 | Ito et al. |
| 7,781,628 B2 | 8/2010 | Ito et al. |
| 7,858,209 B2 | 12/2010 | Lyu et al. |
| 7,993,747 B2 | 8/2011 | Mochizuki et al. |
| 8,013,160 B2 | 9/2011 | Ito et al. |
| 2007/0225454 A1 | 9/2007 | Lewis et al. |

FOREIGN PATENT DOCUMENTS

| | | |
|---|---|---|
| EP | 1892244 B1 | 11/2009 |
| JP | 2007-169535 A | 7/2007 |
| WO | WO 2005/123634 A1 | 12/2005 |

OTHER PUBLICATIONS

Cho et al., "Synthesis and Characterization of Thermally Stable Blue Light-Emitting Polyfluorenes Containing Siloxane Bridges," Macromolecules (2003), vol. 36, pp. 6704-6710.
Extended European Search Report issued May 31, 2013, in European Patent Application No. 13154399.3.
Lee et al., "Synthesis of polyhedral oligomeric silsesquioxane-functionalized polyfluorenes: Hybrid organic-inorganic π-conjugated polymers," Synthetic Metals (2006), vol. 156, pp. 590-596.

*Primary Examiner* — Porfirio Nazario Gonzalez
(74) *Attorney, Agent, or Firm* — Birch, Stewart, Kolasch & Birch, LLP

(57) ABSTRACT

Novel fluorescent compounds having a specific structure are provided. They have improved solubility in organic solvents and compatibility even with low polar resins, especially silicone resins. Using the compounds, transparency fluorescent resin compositions are formulated. Since the fluorescent compound is a single compound, it can be purified to a high purity and has a high fluorescence efficiency.

9 Claims, No Drawings

FLUORESCENT COMPOUND, MAKING METHOD, AND FLUORESCENT RESIN COMPOSITION

CROSS-REFERENCE TO RELATED APPLICATION

This non-provisional application claims priority under 35 U.S.C. §119 (a) on Patent Application No. 2012-027589 filed in Japan on Feb. 10, 2012, the entire contents of which are hereby incorporated by reference.

TECHNICAL FIELD

This invention relates to novel fluorescent compounds, a method of preparing the same, and fluorescent resin compositions.

BACKGROUND ART

Organic compounds having a fluorescent chromophore (to be referred to as "fluorescent compounds", hereinafter) are often used as fluorescent ink or pigment to offer a colorant for paper, fibers and resins partly because they are less expensive than fluorescent inorganic compounds.

The colorants are generally classified into two categories, dyes and pigments. The pigment is an agglomerate of molecules having a chromophore and has a large particle size whereas the dye is a chromophore-containing molecule which is dissolvable in media including solvents and resins. In general, those materials colored with pigments are inferior in transparency, lightness and color saturation to those materials colored with dyes, because the pigment colorants have a larger particle size.

Except fluorescent tags wherein chemical reaction takes place between molecules, fluorescent compounds are generally used as the pigment partly because of improved light resistance and partly because of a low solubility in low polar media.

For the above reason, when resins are colored with fluorescent compounds, relatively high polarity resins like acrylic resins and polyester resins may be colored with dyes. In the case of low polarity resins like polyolefin resins and silicone resins, pigments are inevitably used because dyes are least soluble therein. In the case of coloring with pigments, to obtain transparent resin compositions, the pigment must be finely ground to a size smaller than the wavelength of light and uniformly dispersed in the resin. This grinding/dispersing step consumes a large amount of energy and time.

One method of enhancing compatibility with low polar resins is to attach a fluorescent compound to a resin. For example, Patent Document 1 describes a silicone resin obtained by bonding a fluorescent compound to an amino silicone resin.

A number of fluorescent compounds are known as well as compounds useful as the dye. For example, fluorene compounds with an emission capability of high luminance and efficiency are useful as the luminescent material in organic electroluminescent devices as disclosed in Patent Document 2. Patent Document 3 describes that a compound having an improved solubility in organic solvents is obtainable by linking two fluorene compounds via a siloxanyl group as spacer.

CITATION LIST

Patent Document 1: JP-A 2007-169535
Patent Document 2: WO 2005/123634
Patent Document 3: EP 1892244

DISCLOSURE OF INVENTION

However, the method of Patent Document 1 has the problem that since complete removal of unreacted fluorescent compound is difficult, it will agglomerate and precipitate during storage or service, undesirably inviting changes of the outer appearance and optical properties. Also, the silicone resin, which is a polymeric substance, has a molecular weight distribution and is non-uniform in the chemical structure of every molecule. It is thus difficult that the fluorescent compound is uniformly dispersed within the resin. Where a plurality of fluorescent substituent groups are close to each other within the molecule, there is a possibility of a color tone change upon excimer emission.

The compounds of Patent Document 2 have a low solubility in organic solvents. They are substantially insoluble in low polar solvents and resins such as aliphatic hydrocarbons and silicone resins.

The method of Patent Document 3 achieves an improved solubility in organic solvents, but fails to improve the solubility in low polar solvents and resins such as aliphatic hydrocarbons and silicone resins. It is difficult to use the relevant compounds in these solvents and resins as dye or fluorescent substance.

An object of the invention is to provide a fluorescent compound having an improved solubility in organic solvents, improved compatibility with resins, prepolymers, and monomers, especially silicone resins; a method of preparing the fluorescent compound; and a fluorescent resin composition which can be conveniently prepared using the fluorescent compound.

The inventors have discovered novel fluorescent compounds having a specific structure. The above problems are overcome using these compounds.

In one aspect, the invention provides a fluorescent compound having the general formula (1).

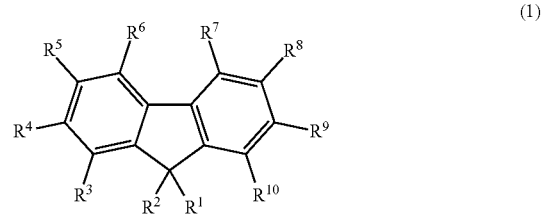

(1)

Herein $R^1$ to $R^{10}$ are each independently a substituent group selected from the group consisting of a straight, branched or cyclic, monovalent $C_1$-$C_{20}$ hydrocarbon group, $C_1$-$C_{20}$ alkoxy group, $C_6$-$C_{20}$ aryloxy group, halogen, hydrogen, amino, cyano and siloxane-containing group having the formula (2), a pair of $R^1$ and $R^2$, $R^3$ and $R^4$, $R^4$ and $R^9$, $R^5$ and $R^6$, $R^7$ and $R^6$, $R^8$ and $R^9$, or $R^9$ and $R^{10}$ may bond together to form a ring structure of 5 to 8 carbon atoms with the carbon atoms to which they are attached, at least one of $R^1$ to $R^{10}$ is a siloxane-containing group having the formula (2).

(2)

Herein Sx is a straight, branched or cyclic organosiloxanyl group of 2 to 10 silicon atoms having a $C_1$-$C_{20}$ monovalent hydrocarbon group bonded to a silicon atom, a silicon atom in Sx being bonded to A, and A is a single bond or a straight, branched or cyclic, divalent $C_1$-$C_{20}$ hydrocarbon group which may contain at least one —O—, —S— or —NR— or a combination thereof, with the proviso that two heteroatoms of oxygen, sulfur and nitrogen are not vicinal except for the cyclic divalent hydrocarbon group, and R is a monovalent $C_1$-$C_{20}$ hydrocarbon group.

In preferred embodiments, the siloxane-containing group having formula (2) contains at least 5 silicon atoms in total; $R^1$ and/or $R^2$ in formula (1) is a siloxane-containing group having formula (2); and $R^4$ and/or $R^9$ in formula (1) is biphenyl.

In a second aspect, the invention provides a fluorescent resin composition comprising the fluorescent compound defined above and a resin. The resin is typically a silicone resin.

In a third aspect, the invention provides a method for preparing a fluorescent compound having formula (1'), comprising reacting an olefin compound having the general formula (3) with a SiH-containing siloxane compound having the general formula (4) in the presence of a platinum catalyst.

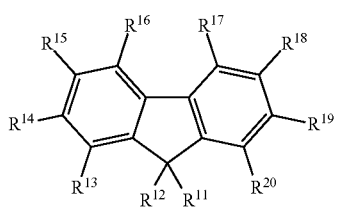

(3)

Herein $R^{11}$ to $R^{20}$ are each independently a substituent group selected from the group consisting of a straight, branched or cyclic, monovalent $C_1$-$C_{20}$ hydrocarbon group, $C_1$-$C_{20}$ alkoxy group, $C_6$-$C_{20}$ aryloxy group, halogen, hydrogen, amino, and cyano group, a pair of $R^{11}$ and $R^{12}$, $R^{13}$ and $R^{14}$, $R^{14}$ and $R^{15}$, $R^{15}$ and $R^{16}$, $R^{17}$ and $R^{18}$, $R^{18}$ and $R^{19}$, or $R^{19}$ and $R^{20}$ may bond together to form a ring structure of 5 to 8 carbon atoms with the carbon atoms to which they are attached, at least one of $R^{11}$ to $R^{20}$ is a monovalent $C_2$-$C_{20}$ hydrocarbon group which is terminated with an aliphatic carbon-carbon unsaturated bond and which may contain at least one —O—, —S— or —NR— or a combination thereof, with the proviso that two heteroatoms of oxygen, sulfur and nitrogen are not vicinal except for the cyclic monovalent hydrocarbon group, R is a monovalent $C_1$-$C_{20}$ hydrocarbon group.

Sx-H (4)

Herein Sx is a straight, branched or cyclic organosiloxanyl group of 2 to 10 silicon atoms having a $C_1$-$C_{20}$ monovalent hydrocarbon group bonded to a silicon atom.

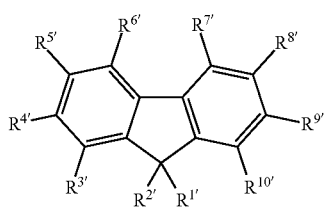

(1')

Herein $R^{1'}$ to $R^{10'}$ are each independently a substituent group selected from the group consisting of a straight, branched or cyclic, monovalent $C_1$-$C_{20}$ hydrocarbon group, $C_1$-$C_{20}$ alkoxy group, $C_6$-$C_{20}$ aryloxy group, halogen, hydrogen, amino, cyano and siloxane-containing group having the formula (2'), a pair of $R^{1'}$ and $R^{2'}$, $R^{3'}$ and $R^{4'}$, $R^{4'}$ and $R^{5'}$, $R^{5'}$ and $R^{6'}$, $R^{7'}$ and $R^{8'}$, $R^{8'}$ and $R^{9'}$, or $R^{9'}$ and $R^{10'}$ may bond together to form a ring structure of 5 to 8 carbon atoms with the carbon atoms to which they are attached, at least one of $R^{1'}$ to $R^{10'}$ is a siloxane-containing group having the formula (2').

Sx-A'- (2')

Herein Sx is a straight, branched or cyclic organosiloxanyl group of 2 to 10 silicon atoms having a $C_1$-$C_{20}$ monovalent hydrocarbon group bonded to a silicon atom, a silicon atom in Sx being bonded to A', and A' is a straight, branched or cyclic, divalent $C_2$-$C_{20}$ hydrocarbon group which may contain at least one —O—, —S— or —NR— or a combination thereof, with the proviso that two heteroatoms of oxygen, sulfur and nitrogen are not vicinal except for the cyclic divalent hydrocarbon group, and R is a monovalent $C_1$-$C_{20}$ hydrocarbon group.

ADVANTAGEOUS EFFECTS OF INVENTION

By virtue of improved compatibility with organic solvents and resins, the fluorescent compounds can be uniformly dispersed in various media. Using the compounds, fluorescent resin compositions having high transparency, lightness and color saturation are readily formulated. Since the fluorescent compound is a single compound without a molecular weight distribution, it can be purified to a high purity and has a high fluorescence efficiency.

DESCRIPTION OF PREFERRED EMBODIMENTS

As used herein, the singular forms "a," "an" and "the" include plural referents unless the context clearly dictates otherwise. The notation (Cn-Cm) means a group containing from n to m carbon atoms per group.

One embodiment of the invention is a fluorescent compound having the general formula (1).

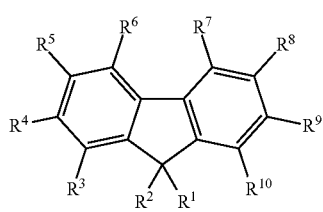

(1)

Herein $R^1$ to $R^{10}$ may be the same or different. Each of $R^1$ to $R^{10}$ is a substituent group selected from among straight, branched or cyclic, monovalent hydrocarbon groups of 1 to 20 carbon atoms, preferably 1 to 12 carbon atoms, alkoxy groups of 1 to 20 carbon atoms, preferably 1 to 12 carbon atoms, aryloxy groups of 6 to 20 carbon atoms, preferably 6 to 12 carbon atoms, halogen, hydrogen, amino, cyano and siloxane-containing groups having the formula (2).

Suitable monovalent hydrocarbon groups include saturated hydrocarbon groups, typically straight, branched or cyclic alkyl groups such as methyl, ethyl, propyl, isopropyl, butyl, isobutyl, sec-butyl, tert-butyl, pentyl, cyclopentyl, isopentyl, 2-pentyl, 3-pentyl, tert-pentyl, hexyl, cyclohexyl, heptyl, octyl, nonyl, decyl, undecyl, dodecyl, tetradecyl, hexadecyl, octadecyl, and eicosyl; unsaturated hydrocarbon groups, typically alkenyl and alkynyl groups such as vinyl, allyl, propenyl, 1-methylpropenyl, butenyl, pentenyl, hexenyl, heptenyl, octenyl, nonenyl, decenyl, undecenyl, and octadecenyl; and aromatic hydrocarbon groups, typically aryl and aralkyl groups such as phenyl, naphthyl, anthryl, phenanthryl, pyrenyl, benzyl, phenethyl, phenylpropyl, 2-methylphenyl, 3-methylphenyl, 4-methylphenyl, 2,4-dimethylphenyl, 3,5-dimethylphenyl, 3,5-di-tert-butylphenyl, and biphenyl. Of these, preferred are methyl, ethyl, propyl, isopropyl, butyl, isobutyl, sec-butyl, tert-butyl, pentyl, hexyl, heptyl, octyl, nonyl, decyl, undecyl, dodecyl, vinyl, allyl and phenyl. Suitable alkoxy groups include methoxy, ethoxy, butoxy, tert-butoxy, and hexyloxy. Suitable aryloxy groups include phenoxy, p-methylphenoxy and naphthoxy. Suitable halogen atoms include fluorine, chlorine, bromine and iodine. Suitable amino groups include dimethylamino and diethylamino.

In formula (1), a pair of $R^1$ and $R^2$, $R^3$ and $R^4$, $R^4$ and $R^5$, $R^5$ and $R^6$, $R^7$ and $R^8$, $R^8$ and $R^9$, or $R^9$ and $R^{10}$ may bond together to form an alicyclic or aromatic ring structure of 5 to 8 carbon atoms with the carbon atom or atoms to which they are attached. In this case, the structure of formula (1) forms a fused ring structure as represented by the following formulae (1a) to (1 g). Where a ring structure is formed, $R^{1a}$, $R^{2a}$, $R^{3a}$, $R^{4a}$, $R^{5a}$, $R^{6a}$, $R^{7a}$, $R^{8a}$, $R^{9a}$, and $R^{10a}$ in the following formulae are di- or trivalent groups obtained by eliminating one or two hydrogen atoms from $R^1$, $R^2$, $R^3$, $R^4$, $R^5$, $R^6$, $R^7$, $R^8$, $R^9$, and $R^{10}$, respectively.

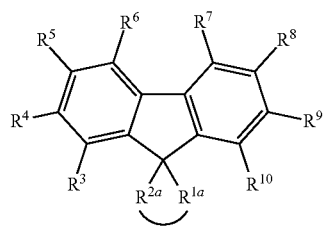

(1a)

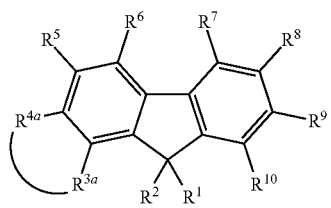

(1b)

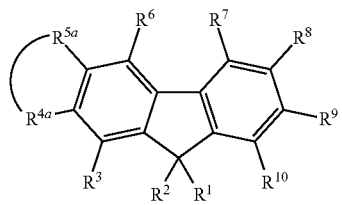

(1c)

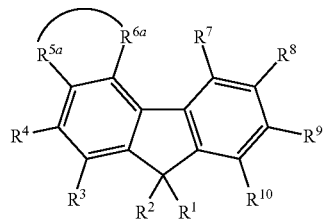

(1d)

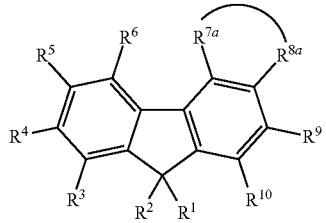

(1e)

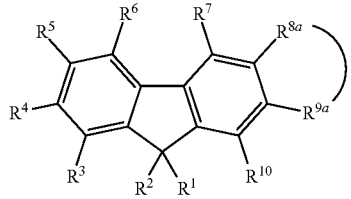

(1f)

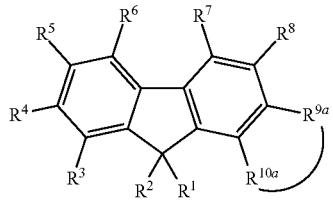

(1g)

In formula (1), at least one of $R^1$ to $R^{10}$, especially $R^1$ and/or $R^2$ is a siloxane-containing group having the following formula (2). Accordingly, the compound of formula (1) contains at least one group having formula (2). In this embodiment, it is preferred that $R^1$ and/or $R^2$ be a group having formula (2). The total number of silicon atoms in formula (1) is preferably at least 2, more preferably at least 5. If the number of silicon atoms is less than 2, the compound may not have a sufficient solubility. Although the upper limit of silicon count is not critical, the silicon count is preferably up to 10. It is also preferred that $R^4$ and/or $R^9$ be biphenyl.

$$Sx-A- \quad (2)$$

In formula (2), Sx is a straight, branched or cyclic organosiloxanyl group of 2 to 10 silicon atoms, preferably 3 to 10 silicon atoms, more preferably 5 to 10 silicon atoms, having a monovalent hydrocarbon group of 1 to 20 carbon atoms, especially 1 to 6 carbon atoms, typically alkyl, bonded to a silicon atom. A silicon atom in Sx is bonded to A. Sx is free of a reactive substituent group like a silicon-hydrogen bond or silicon-alkoxy linkage.

Suitable monovalent hydrocarbon groups to be bonded to a silicon atom include alkyl groups such as methyl, ethyl, propyl, isopropyl, butyl, sec-butyl and tert-butyl, cycloalkyl groups such as cyclohexyl, aryl groups such as phenyl and tolyl, alkenyl groups such as vinyl, allyl, propenyl and butenyl, and alkynyl groups such as ethynyl, propynyl and butynyl.

Examples of Sx include linear organosiloxanyl groups such as pentamethyldisiloxan-1-yl, 3,3,3-triethyl-1,1-dimethyldisiloxan-1-yl, pentaethyldisiloxan-1-yl, 3-vinyl-1,1,3,3-tetramethyldisiloxan-1-yl, 3-tert-butyl-1,1,3,3-tetramethyldisiloxan-1-yl, 3,3,3-triisopropyl-1,1-dimethyldisiloxan-1-yl, 1,1-diphenyl-3,3,3-trimethyldisiloxan-1-yl, 3-methyl-1,1,3,3-tetraphenyldisiloxan-1-yl, 1-cyclohexyl-1,3,3,3-tetramethyldisiloxan-1-yl, heptamethyltrisiloxan-1-yl, nonamethyltetrasiloxan-1-yl, undecamethylpentasiloxan-1-yl, tridecamethylhexasiloxan-1-yl, pentadecamethylheptasiloxan-1-yl, heptadecamethyloctasiloxan-1-yl, nonadecamethylnonasiloxan-1-yl, and heneicosamethyldecasiloxan-1-yl;

branched organosiloxanyl groups such as 1-trimethylsiloxy-1,3,3,3-tetramethyldisiloxan-1-yl, 1-trimethylsiloxy-1,3,3,5,5,5-hexamethyltrisiloxan-1-yl, 1-pentamethyldisiloxanyloxy-1,3,3,5,5,5-hexamethyltrisiloxan-1-yl, 1-trimethylsiloxy-1,3,3,5,5,7,7,7-octamethyltetrasiloxan-1-yl, and 1,1-bis(trimethylsiloxy)-3,3,3-trimethyldisiloxan-1-yl;

cyclic organosiloxanyl groups such as 1,3,3,5,5,7,7-heptamethylcyclotetrasiloxan-1-yl and 1,3,5,7-tetramethyl-1,3,5,7-tetravinylcyclotetrasiloxan-1-yl.

Of these, preferred are pentamethyldisiloxan-1-yl, heptamethyltrisiloxan-1-yl, nonamethyltetrasiloxan-1-yl, undecamethylpentasiloxan-1-yl, 1-trimethylsiloxy-1,3,3,3-tetramethyldisiloxan-1-yl, and 1,3,3,5,5,7,7-heptamethylcyclotetrasiloxan-1-yl.

In formula (2), A is a single bond or a straight, branched or cyclic, divalent hydrocarbon group of 1 to 20 carbon atoms, preferably 1 to 12 carbon atoms, which may contain at least one —O—, —S— or —NR— or a combination thereof in a discontinuous manner, with the proviso that two heteroatoms of oxygen, sulfur and nitrogen are not vicinal except for the cyclic divalent hydrocarbon group.

R is a monovalent hydrocarbon group of 1 to 20 carbon atoms, preferably 1 to 12 carbon atoms. Suitable monovalent hydrocarbon groups include saturated hydrocarbon groups, typically straight, branched or cyclic alkyl groups such as methyl, ethyl, propyl, isopropyl, butyl, isobutyl, sec-butyl, tert-butyl, pentyl, cyclopentyl, isopentyl, 2-pentyl, 3-pentyl, tert-pentyl, hexyl, cyclohexyl, octyl, decyl, dodecyl, tetradecyl, hexadecyl, octadecyl, and eicosyl; unsaturated hydrocarbon groups, typically alkenyl and alkynyl groups such as vinyl, allyl, propenyl, 1-methylpropenyl, butenyl, pentenyl, hexenyl, heptenyl, octenyl, nonenyl, decenyl, undecenyl, and octadecenyl; and aromatic hydrocarbon groups, typically aryl and aralkyl groups such as phenyl, naphthyl, benzyl, phenethyl, phenylpropyl, 2-methylphenyl, 3-methylphenyl, 4-methylphenyl, 2,4-dimethylphenyl, 3,5-dimethylphenyl, and 3,5-di-tert-butylphenyl. Of these, preferred are methyl, ethyl, propyl, isopropyl, butyl, isobutyl, sec-butyl, tert-butyl, pentyl, hexyl, octyl, decyl, dodecyl, vinyl, allyl and phenyl.

Suitable divalent hydrocarbon groups represented by A include straight, branched or cyclic aliphatic divalent hydrocarbon groups such as methylene, 1,2-ethanediyl, 1,1-ethanediyl, 1,2-ethenediyl, 1,1-ethenediyl, 1,3-propanediyl, 1,2-propanediyl, 2-methyl-1,3-propanediyl, 1,3-butanediyl, 1,4-butanediyl, 1,5-pentanediyl, 1,6-hexanediyl, 1,4-cyclohexanediyl, 1,7-heptanediyl, 1,8-octanediyl, 1,9-nonanediyl, 1,10-decanedlyl, 1,11-undecanediyl, 1,12-dodecanedlyl, 1,13-tridecanediyl, 1,14-tetradecanediyl, 1,15-pentadecanediyl, 1,16-hexadecanediyl, 1,17-heptadecanedlyl, 1,18-octadecanediyl, 1,19-nonadecanediyl, and 1,20-eicosanedlyl;

aromatic divalent hydrocarbon groups such as 1,3-benzenediyl, 1,4-benzenediyl, 2-methyl-1,4-benzenediyl, 3-methyl-1,4-benzenediyl, 2,5-dimethyl-1,4-benzenediyl, 3-propylbenzen-1-yl, 4-propylbenzene-1-yl, 1,8-naphthalenedlyl, 2,7-naphthalenediyl, 1,3-naphthalenedlyl, 1,4-naphthalenediyl, 1,3-anthracenediyl, 1,4-anthracenediyl, 1,5-anthracenediyl, 2,6-anthracenediyl, 9,10-anthracenediyl, 1,6-pyrenediyl, 1,8-pyrenediyl, 2,7-pyrenediyl, 4,9-pyrenediyl, 4-ethylbenzene-1,2'-diyl, 4-propylbenzene-1,3'-diyl, 4,4'-biphenyldiyl, 4,3'-biphenyldiyl, 3'-propylbiphenyl-4-yl, and 4'-propylbiphenyl-4-yl; and heteroatom-containing divalent hydrocarbon groups such as 2-oxa-1,3-propanediyl, 3-oxa-1,5-pentanediyl, 3-oxa-2-methyl-1,5-pentanediyl, 3-oxa-1,6-hexanediyl, 3-oxa-2-methyl-1,6-hexanediyl, 3-oxa-2-methyl-1,6-hexanediyl, 3,6-dioxa-1,8-octanediyl, 3,7-dioxa-1,9-nonanediyl, 3-methyl-3-aza-1,5-pentanediyl, 3-methyl-3-aza-1,6-hexanediyl, 3-phenyl-3-aza-1,6-hexanediyl, 3-methyl-3-aza-7-oxa-1,9-nonanediyl, 3-thia-1,5-pentanediyl, 3,6-dithia-1,8-octanediyl, 2,5-furanediyl, 2,5-thiophenediyl, 1,2,4-oxadiazole-3,5-diyl, 1,3,4-oxadiazole-2,5-diyl, 1,2,4-thiadiazole-3,5-diyl, and 1,3,4-thiadiazole-2,5-diyl. Of these, preferred are methylene, 1,2-ethanediyl, 1,3-propanediyl, 2-methyl-1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, and 1,11-undecanediyl.

In formula (2), an arbitrary combination of Sx with A is possible. Suitable siloxane-containing groups of formula (2) wherein Sx is undecamethylpentasiloxan-1-yl, for example, include substituted hydrocarbon groups such as undecamethylpentasiloxan-1-yl, undecamethylpentasiloxan-1-ylmethyl, 2-(undecamethylpentasiloxan-1-yl)ethyl, 1-(undecamethylpentasiloxan-1-yl)ethyl, 2-(undecamethylpentasiloxan-1-yl)ethenyl, 3-(undecamethylpentasiloxan-1-yl)propyl, 2-methyl-3-(undecamethylpentasiloxan-1-yl)propyl, 4-(undecamethylpentasiloxan-1-yl)butyl, 5-(undecamethylpentasiloxan-1-yl)pentyl, 6-(undecamethylpentasiloxan-1-yl)hexyl, 7-(undecamethylpentasiloxan-1-yl)heptyl, 8-(undecamethylpentasiloxan-1-yl)octyl, 9-(undecamethylpentasiloxan-1-yl)nonyl, 10-(undecamethylpentasiloxan-1-yl)decyl, 11-(undecamethylpentasiloxan-1-yl)undecyl, 12-(undecamethylpentasiloxan-1-yl)dodecyl, 14-(undecamethylpentasiloxan-1-yl)tetradecyl, 16-(undecamethylpentasiloxan-1-yl)hexadecyl, 18-(undecamethylpentasiloxan-1-yl)octadecyl, 20-(undecamethylpentasiloxan-1-yl)eicosyl, 4-(undecamethylpentasiloxan-1-yl)phenyl, 3-(undecamethylpentasiloxan-1-yl)phenyl, 4-[2-(undecamethylpentasiloxan-1-yl)ethyl]phenyl, 4-[3-(undecamethylpentasiloxan-1-yl)propyl]phenyl, 4-[2-(undecamethylpentasiloxan-1-yl)propyl]phenyl, 2-{2-(undecamethylpentasiloxan-1-yl)ethoxy}ethyl, 3-{2-(undecamethylpentasiloxan-1-yl)ethoxy}propyl, 2-{3-(undecamethylpentasiloxan-1-yl)propoxy}ethyl, 2-{3-(undecamethylpentasiloxan-1-yl)propoxy}propyl, 2-{2-{3-(undecamethylpentasiloxan-1-yl)propoxy}ethoxy}ethyl, 2-{2-{3-(undecamethylpentasiloxan-1-yl)propoxy}propoxy}ethyl, and 2-{2-{3-(undecamethylpentasiloxan-1-yl)propoxy}propoxy}propyl;

substituted organoxy groups such as (undecamethylpentasiloxan-1-yl)methoxy, 2-(undecamethylpentasiloxan-1-yl)ethoxy, 3-(undecamethylpentasiloxan-1-yl)propoxy, 2-methyl-3-(undecamethylpentasiloxan-1-yl)propoxy, 3-(undecamethylpentasiloxan-1-yl)butoxy, 4-(undecamethylpentasiloxan-1-yl)butoxy, 4-(undecamethylpentasiloxan-1-yl)phenoxy, 2-{2-(undecamethylpentasiloxan-1-yl)ethoxy}ethoxy, 3-{2-(undecamethylpentasiloxan-1-yl)ethoxy}propoxy, 2-{3-(undecamethylpentasiloxan-1-yl)propoxy}ethoxy, 2-{3-(undecamethylpentasiloxan-1-yl)propoxy}propoxy, 2-{2-{3-(undecamethylpentasiloxan-1-yl)propoxy}ethoxy}ethoxy, 2-{2-{3-(undecamethylpentasiloxan-1-yl)propoxy}propoxy}ethoxy, 2-{2-{3-(undecamethylpentasiloxan-1-yl)propoxy}propoxy}propoxy, 2-[N-methyl-N-{3-(undecamethylpentasiloxan-1-yl)propyl}amino]-ethoxy, 2-[N-methyl-N-{3-(undecamethylpentasiloxan-1-yl)propyl}amino]-ethoxy, 1-methyl-2-[N-methyl-N-{3-

(undecamethylpentasiloxan-1-yl)-propyl}amino]ethoxy, and 2-[(2-(undecamethylpentasiloxan-1-yl)ethylsulfanyl]ethoxy;

substituted organoxycarbonyl groups such as (undecamethylpentasiloxan-1-yl)methoxycarbonyl, 2-(undecamethylpentasiloxan-1-yl)ethoxycarbonyl, 3-(undecamethylpentasiloxan-1-yl)propoxycarbonyl, 2-methyl-3-(undecamethylpentasiloxan-1-yl)propoxycarbonyl, 3-(undecamethylpentasiloxan-1-yl)butoxycarbonyl, 4-(undecamethylpentasiloxan-1-yl)phenoxycarbonyl, 2-{2-(undecamethylpentasiloxan-1-yl)ethoxy}ethoxycarbonyl, 3-{2-(undecamethylpentasiloxan-1-yl)ethoxy}propoxycarbonyl, 2-{(3-(undecamethylpentasiloxan-1-yl)propoxy}ethoxycarbonyl, 2-{(3-(undecamethylpentasiloxan-1-yl)propoxy}propoxycarbonyl, 2-{2-{(3-(undecamethylpentasiloxan-1-yl)propoxy}ethoxy}-ethoxycarbonyl, 2-{(2-{(3-(undecamethylpentasiloxan-1-yl)propoxy}propoxy}-ethoxycarbonyl, 2-{(2-{(3-(undecamethylpentasiloxan-1-yl)propoxy}propoxy}-propoxycarbonyl, 2-[N-methyl-N-{3-(undecamethylpentasiloxan-1-yl)propyl}-amino]ethoxycarbonyl, 2-[N-methyl-N-{3-(undecamethylpentasiloxan-1-yl)propyl}-amino]ethoxycarbonyl, 1-methyl-2-[N-methyl-N-{3-(undecamethylpentasiloxan-1-yl)-propyl}amino]ethoxycarbonyl, and 2-{2-(undecamethylpentasiloxan-1-yl)ethylsulfanyl}ethoxycarbonyl; and substituted acyloxy groups such as (undecamethylpentasiloxan-1-yl)acetoxy, 3-(undecamethylpentasiloxan-1-yl)propionyloxy, 2-methyl-3-(undecamethylpentasiloxan-1-yl)propionyloxy, 5-(undecamethylpentasiloxan-1-yl)pentanoyloxy, 6-(undecamethylpentasiloxan-1-yl)hexanoyloxy, 11-(undecamethylpentasiloxan-1-yl)undecanoyloxy, 4-(undecamethylpentasiloxan-1-yl)benzoyloxy, {2-(undecamethylpentasiloxan-1-yl)ethoxy}acetyl, 3-{2-(undecamethylpentasiloxan-1-yl)ethoxy}propionyloxy, (3-(undecamethylpentasiloxan-1-yl)propoxy)acetoxy, 3-{3-(undecamethylpentasiloxan-1-yl)propoxy}propionyloxy, {2-{3-(undecamethylpentasiloxan-1-yl)propoxy}ethoxy}acetoxy, {2-{3-(undecamethylpentasiloxan-1-yl)propoxy}propoxy}acetoxy, 3-[N-methyl-N-{3-(undecamethylpentasiloxan-1-yl)propyl}-amino]propionyloxy, and 3-[(N-methyl-N-{3-(undecamethylpentasiloxan-1-yl)propyl}-amino]propionyloxy.

Of the groups having formula (2), combinations of preferred examples of Sx with preferred examples of A are preferred. Preferred groups include 3-(pentamethyldisiloxan-1-yl)propyl, 3-(heptamethyltrisiloxan-1-yl)propyl, 3-(nonamethyltetrasiloxan-1-yl)propyl, 3-(undecamethylpentasiloxan-1-yl)propyl, 3-(1-trimethylsiloxy-1,3,3,3-tetramethyldisiloxan-1-yl)propyl, 3-(1,3,3,5,5,7,7-heptamethylcyclotetrasiloxan-1-yl)propyl, 4-(pentamethyldisiloxan-1-yl)butyl, 4-(heptamethyltrisiloxan-1-yl)butyl, 3-(nonamethyltetrasiloxan-1-yl)butyl, 4-(undecamethylpentasiloxan-1-yl)butyl, 4-(1-trimethylsiloxy-1,3,3,3-tetramethyldisiloxan-1-yl)butyl, 4-(1,3,3,5,5,7,7-heptamethylcyclotetrasiloxan-1-yl)butyl, 5-(pentamethyldisiloxan-1-yl)pentyl, 5-(heptamethyltrisiloxan-1-yl)pentyl, 5-(nonamethyltetrasiloxan-1-yl)pentyl, 5-(undecamethylpentasiloxan-1-yl)pentyl, 5-(1-trimethylsiloxy-1,3,3,3-tetramethyldisiloxan-1-yl)pentyl, 5-(1,3,3,5,5,7,7-heptamethylcyclotetrasiloxan-1-yl)pentyl, 6-(pentamethyldisiloxan-1-yl)hexyl, 6-(heptamethyltrisiloxan-1-yl)hexyl, 6-(nonamethyltetrasiloxan-1-yl)hexyl, 6-(undecamethylpentasiloxan-1-yl)pentyl, 6-(1-trimethylsiloxy-1,3,3,3-tetramethyldisiloxan-1-yl)hexyl, 6-(1,3,3,5,5,7,7-heptamethylcyclotetrasiloxan-1-yl)hexyl, 7-(pentamethyldisiloxan-1-yl)heptyl, 7-(heptamethyltrisiloxan-1-yl)heptyl, 7-(nonamethyltetrasiloxan-1-yl)heptyl, 7-(undecamethylpentasiloxan-1-yl)heptyl, 7-(1-trimethylsiloxy-1,3,3,3-tetramethyldisiloxan-1-yl)heptyl, 7-(1,3,3,5,5,7,7-heptamethylcyclotetrasiloxan-1-yl)heptyl, 8-(pentamethyldisiloxan-1-yl)octyl, 8-(heptamethyltrisiloxan-1-yl)octyl, 8-(nonamethyltetrasiloxan-1-yl)octyl, 8-(undecamethylpentasiloxan-1-yl)octyl, 8-(1-trimethylsiloxy-1,3,3,3-tetramethyldisiloxan-1-yl)octyl, 8-(1,3,3,5,5,7,7-heptamethylcyclotetrasiloxan-1-yl)octyl, 9-(pentamethyldisiloxan-1-yl)nonyl, 9-(heptamethyltrisiloxan-1-yl)nonyl, 9-(nonamethyltetrasiloxan-1-yl)nonyl, 9-(undecamethylpentasiloxan-1-yl)nonyl, 9-(1-trimethylsiloxy-1,3,3,3-tetramethyldisiloxan-1-yl)nonyl, 9-(1,3,3,5,5,7,7-heptamethylcyclotetrasiloxan-1-yl)nonyl, 10-(pentamethyldisiloxan-1-yl)decyl, 10-(heptamethyltrisiloxan-1-yl)decyl, 10-(nonamethyltetrasiloxan-1-yl)decyl, 10-(undecamethylpentasiloxan-1-yl)decyl, 10-(1-trimethylsiloxy-1,3,3,3-tetramethyldisiloxan-1-yl)decyl, 10-(1,3,3,5,5,7,7-heptamethylcyclotetrasiloxan-1-yl)decyl, 11-(pentamethyldisiloxan-1-yl)undecyl, 11-(heptamethyltrisiloxan-1-yl)undecyl, 11-(nonamethyltetrasiloxan-1-yl)undecyl, 11-(undecamethylpentasiloxan-1-yl)undecyl, 11-(1-trimethylsiloxy-1,3,3,3-tetramethyldisiloxan-1-yl)-undecyl, and 11-(1,3,3,5,5,7,7-heptamethylcyclotetrasiloxan-1-yl)undecyl.

Illustrative, non-limiting examples of the compound having formula (1) are given below wherein Sx is as defined above.

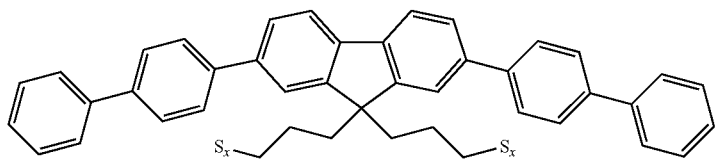

(1-1)

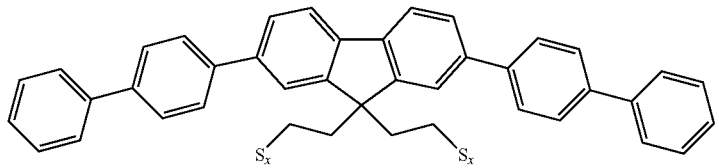

(1-2)

-continued
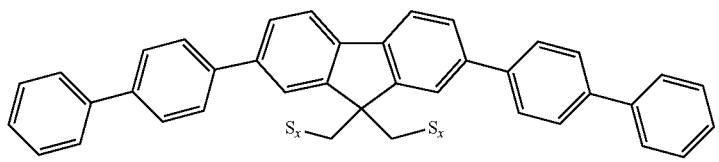
(1-3)
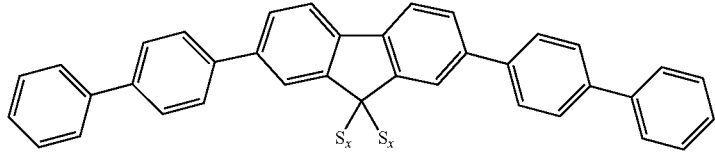
(1-4)
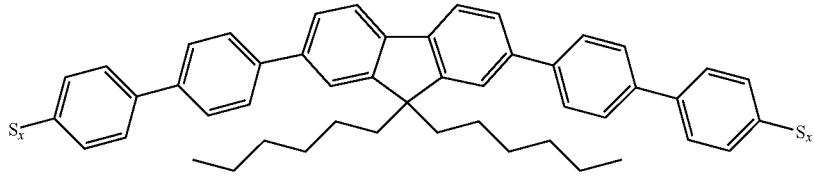
(1-5)
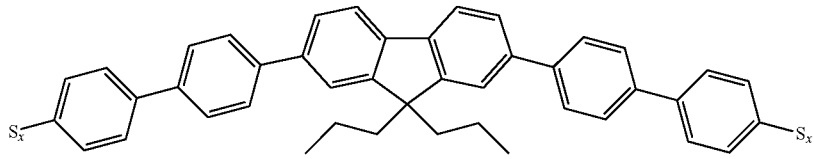
(1-6)
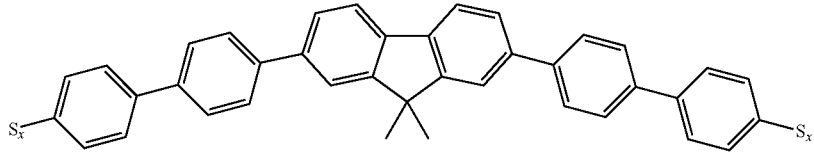
(1-7)
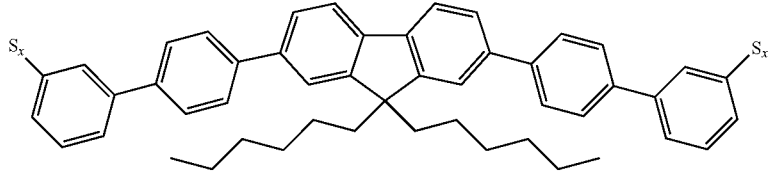
(1-8)
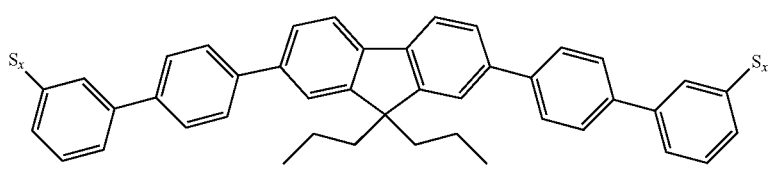
(1-9)
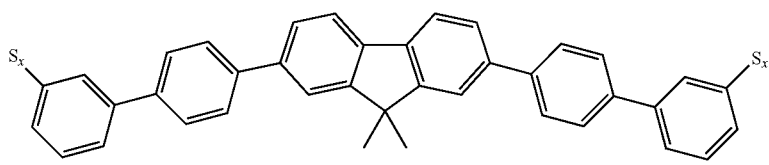
(1-10)
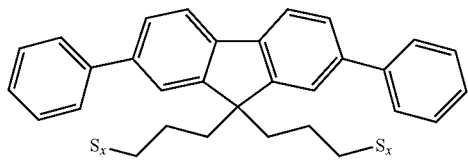
(1-11)
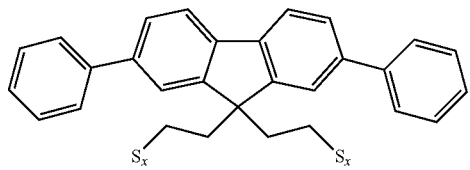
(1-12)

-continued
(1-13)
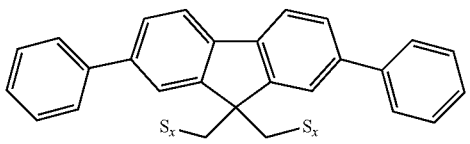
(1-14)
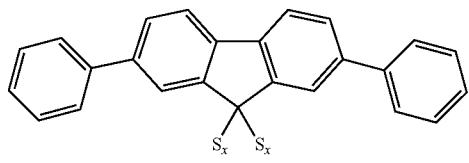
(1-15)
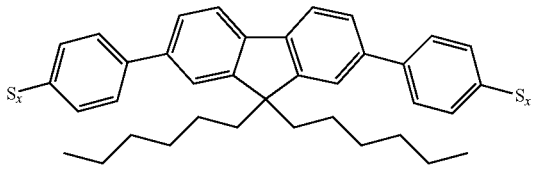
(1-16)
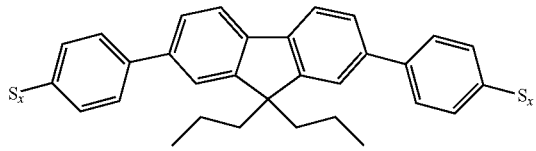
(1-17)
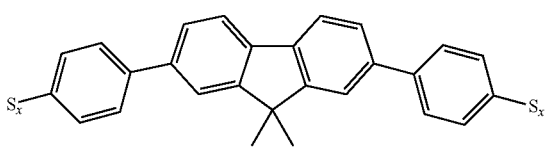
(1-18)
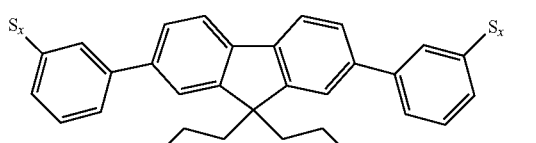
(1-19)
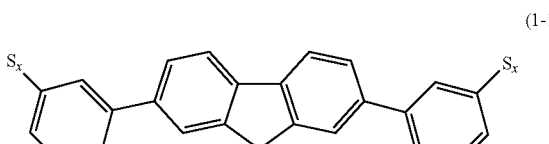
(1-20)
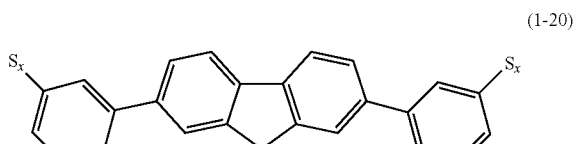
(1-21)
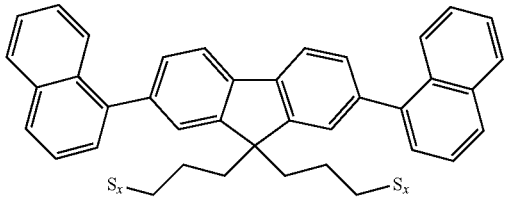
(1-22)
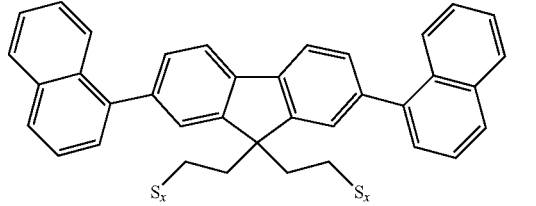
(1-23)
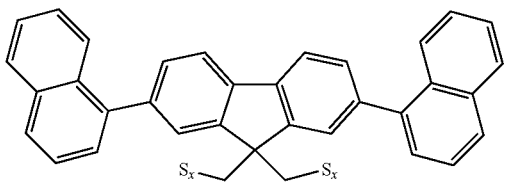
(1-24)
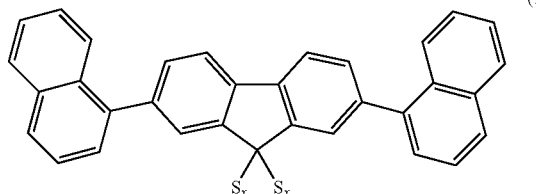
(1-25)
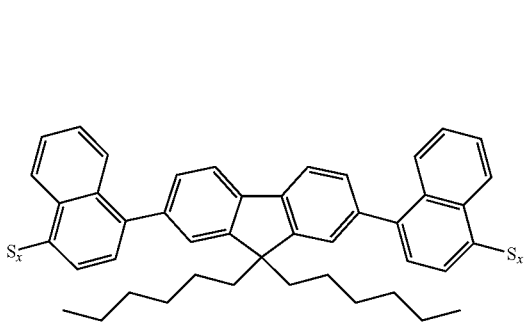
(1-26)
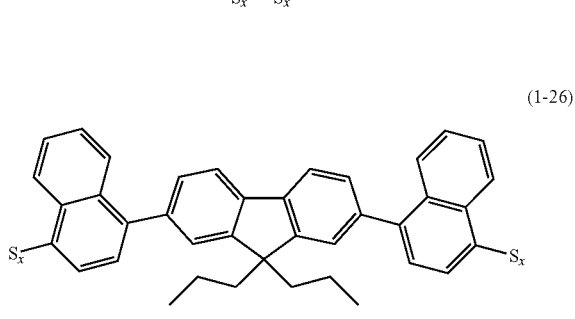

-continued
(1-27)
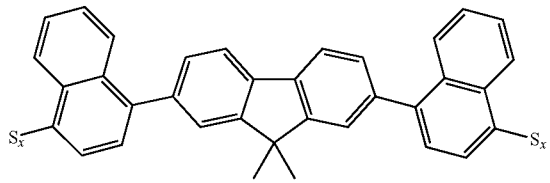
(1-28)
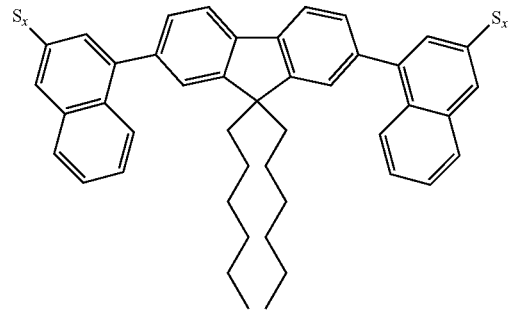
(1-29)
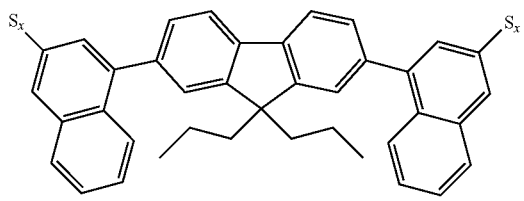
(1-30)
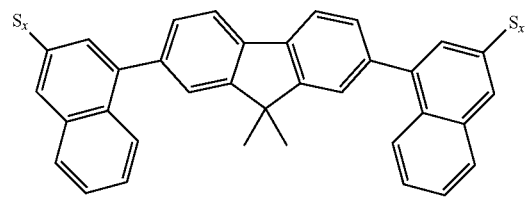
(1-31)
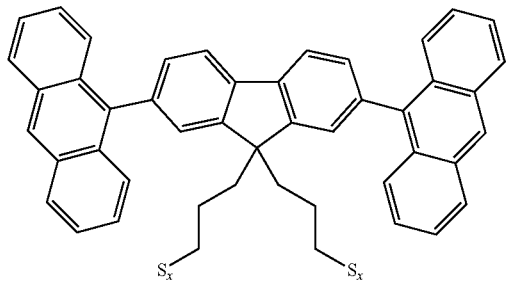
(1-32)
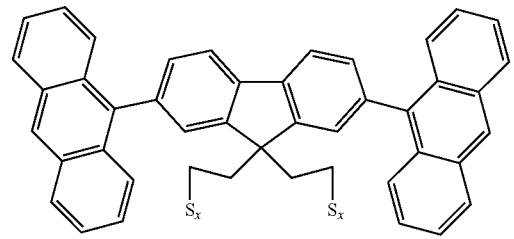
(1-33)
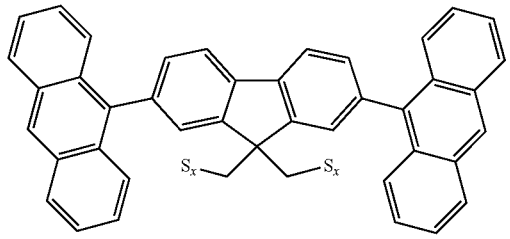
(1-34)
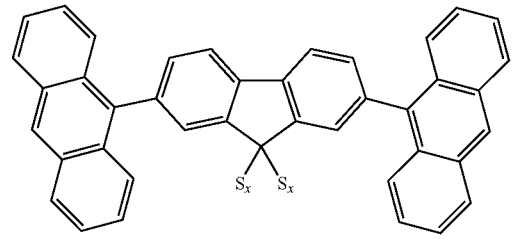
(1-35)
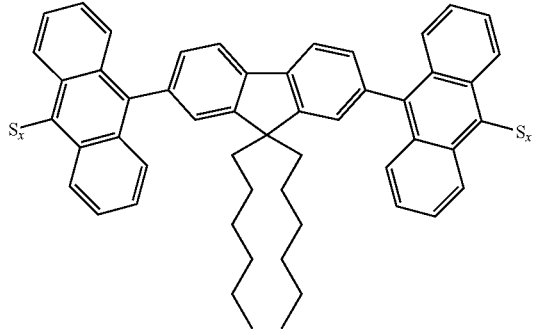
(1-36)
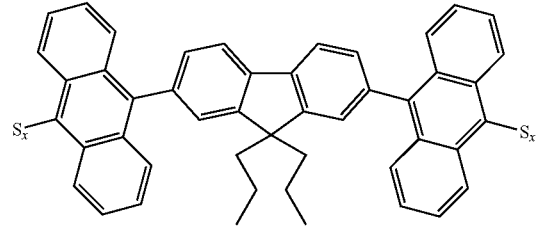

-continued
(1-37)
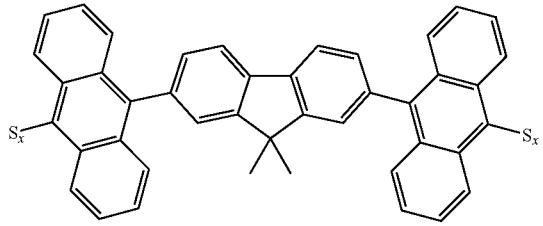
(1-38)
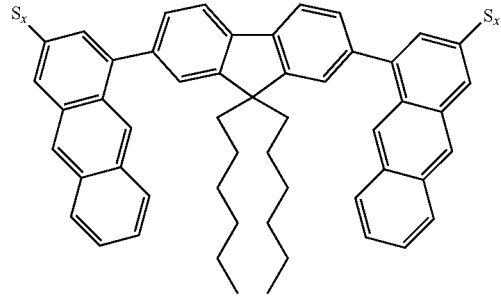
(1-39)
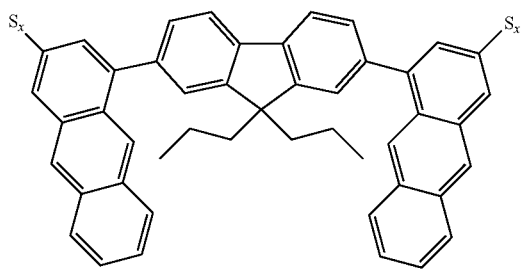
(1-40)
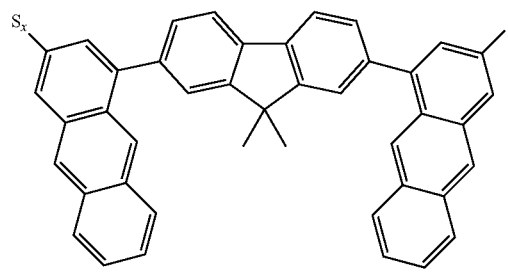
(1-41)
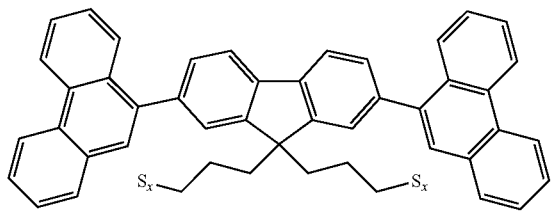
(1-42)
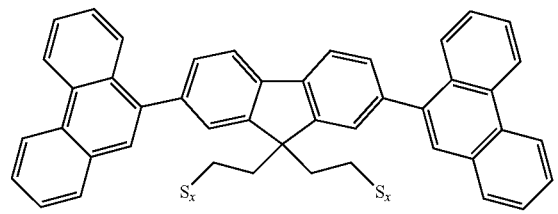
(1-43)
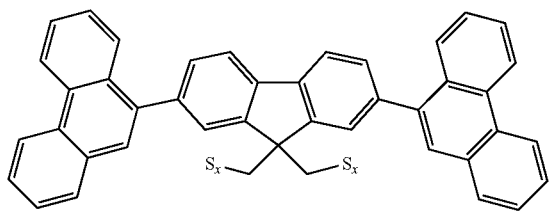
(1-44)
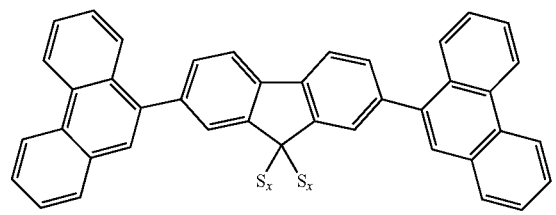
(1-45)
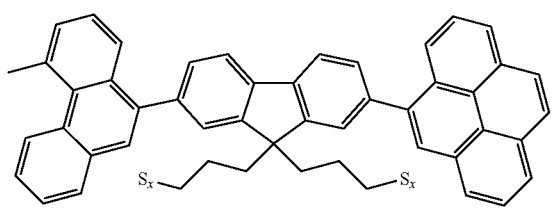
(1-46)
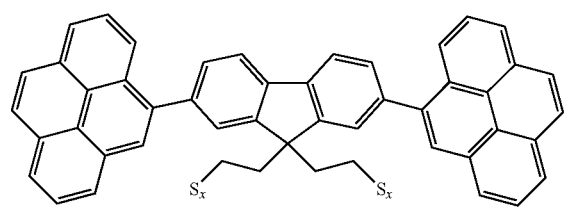
(1-47)
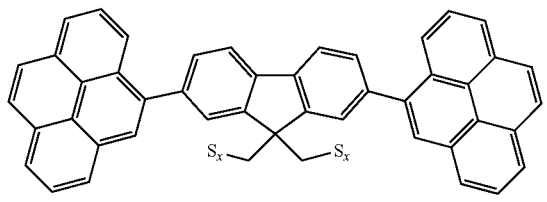
(1-48)
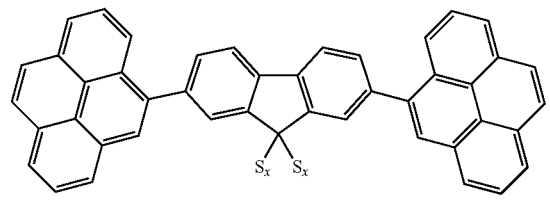

-continued
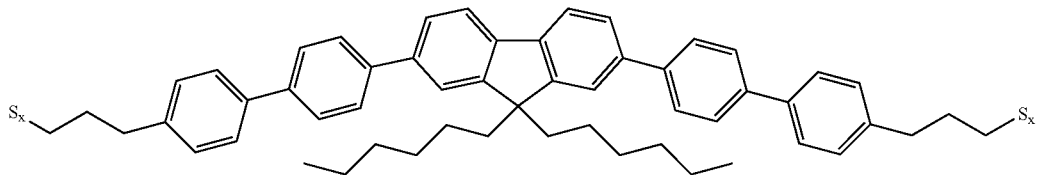 (1-49)
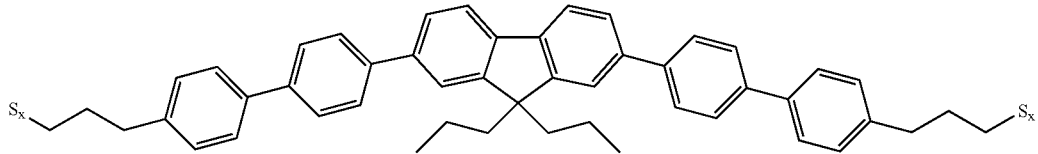 (1-50)
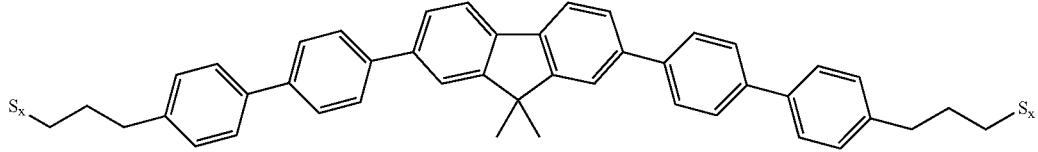 (1-51)
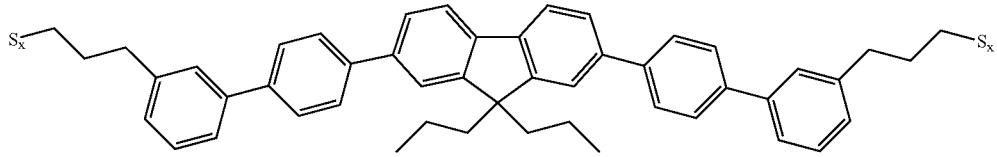 (1-52)
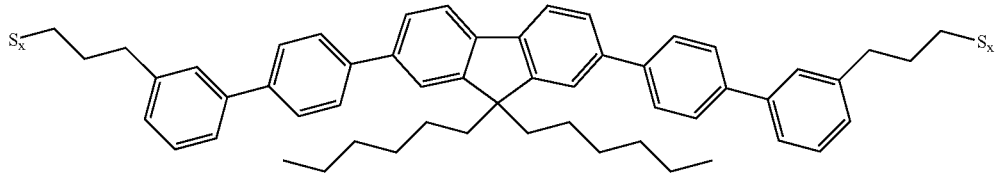 (1-53)
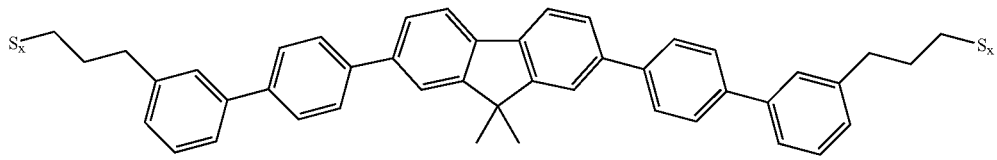 (1-54)
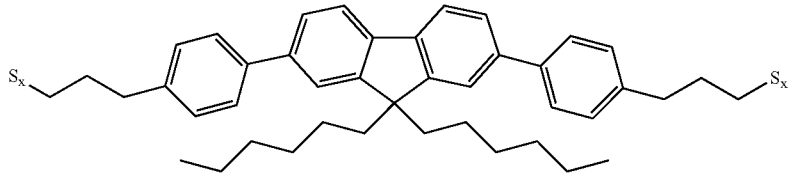 (1-55)
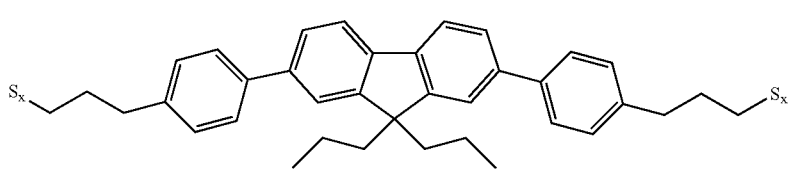 (1-56)
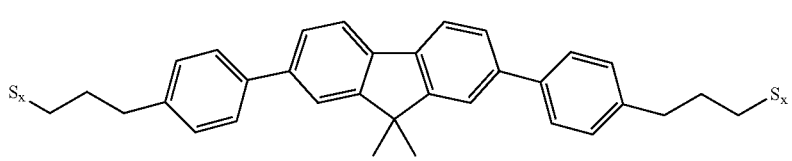 (1-57)

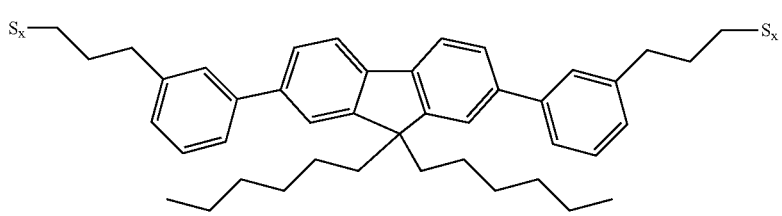

(1-58)

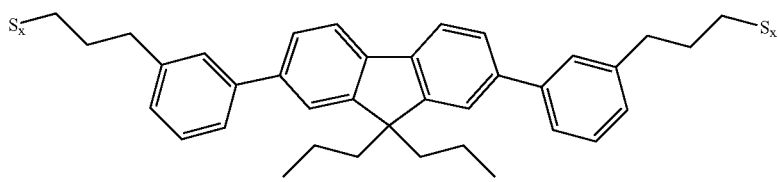

(1-59)

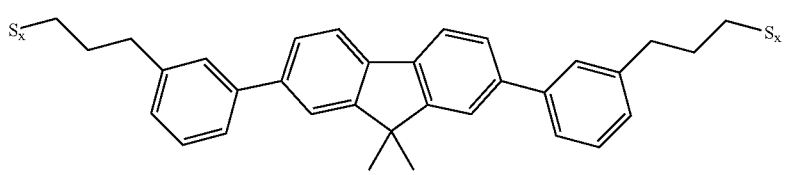

(1-60)

(1-61)

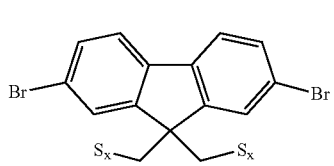

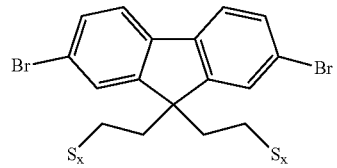

(1-62)

(1-63)

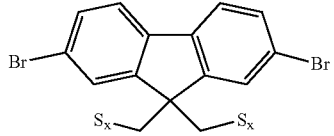

Specifically, suitable compounds having formula (1) include
2,7-dibromo-9,9'-di-[3-(1-trimethylsiloxy-1,3,3,3-tetramethyldisiloxan-1-yl)propyl]fluorene,
2,7-bis(biphenyl)-9,9'-di-[3-(1-trimethylsiloxy-1,3,3,3-tetramethyldisiloxan-1-yl)propyl]fluorene,
2,7-dibromo-9,9'-di-[3-(undecamethylpentasiloxan-1-yl)-propyl]fluorene, and
2,7-bis(biphenyl)-9,9'-di-[3-(undecamethylpentasiloxan-1-yl)-propyl]fluorene.

Although the fluorescent compound having formula (1) contains a siloxane-containing group, it is not a mixture of siloxanes having a molecular weight distribution because the siloxane moiety has a definitely prescribed structure. That is, the compound having formula (1) is a single compound rather than a mixture. Since the molar concentration of fluorescent chromophore is a key factor that governs fluorescent properties of a composition which is prepared using the compound, the single compound form is desirable for accurately determining the molar concentration.

Desirably the fluorescent compound having formula (1) is purified to as high a purity as possible in order that the compound exert its fluorescent properties to a maximum extent. Since the fluorescent compound having formula (1) is a single compound as alluded to just above, it can be purified to a high purity. Any suitable purifying means as applied to ordinary organic compounds may be used, including recrystallization, precipitation, solvent washing, silica gel column chromatography, gel permeation chromatography, and preparative liquid chromatography. The fluorescent compound should preferably have a purity of at least 95%, more preferably at least 98%, and most preferably at least 99%, as purified by liquid chromatography. If a certain amount of impurity is contained, then the fluorescent compound having formula (1) may have somewhat degraded fluorescent properties, and a fluorescent resin composition prepared using the compound may sometimes become cloudy and have degraded fluorescent properties. The purity may be determined by either normal or reversed phase liquid chromatography. For example, Inertsil® Diol columns by GL Sciences Inc. may be used in the normal phase chromatography, and XBridge® C18 columns by Waters Corp. used in the reversed phase chromatography. Size exclusion chromatography is also useful, and TSK-GEL SuperHZ 2000 columns by Tosoh Corp. may be used, for example.

The fluorescent compound may be prepared by bonding a siloxane-containing group to a known fluorene structure. The bonding of a siloxane-containing group may be achieved by hydrosilylation reaction to an aliphatic unsaturated group using a siloxane having a Si—H bond, but not limited thereto.

In one embodiment, the fluorescent compound having formula (1) is prepared by reacting an olefin compound having the general formula (3) with a SiH-containing siloxane compound having the general formula (4) in the presence of a platinum catalyst.

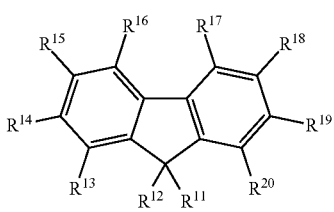

(3)

In formula (3), $R^{11}$ to $R^{20}$ are each independently a substituent group selected from among a straight, branched or cyclic, monovalent hydrocarbon group of 1 to 20 carbon atoms, preferably 1 to 12 carbon atoms, alkoxy group of 1 to 20 carbon atoms, preferably 1 to 12 carbon atoms, aryloxy group of 6 to 20 carbon atoms, preferably 6 to 12 carbon atoms, halogen, hydrogen, amino, and cyano group. A pair of $R^{11}$ and $R^{12}$, $R^{13}$ and $R^{14}$, $R^{14}$ and $R^{15}$, $R^{15}$ and $R^{16}$, $R^{17}$ and $R^{18}$, $R^{18}$ and $R^{19}$, or $R^{19}$ and $R^{20}$ may bond together to form an alicyclic or aromatic ring structure of 5 to 8 carbon atoms with the carbon atom or atoms to which they are attached.

Suitable monovalent hydrocarbon groups include saturated hydrocarbon groups, typically straight, branched or cyclic alkyl groups such as methyl, ethyl, propyl, isopropyl, butyl, isobutyl, sec-butyl, tert-butyl, pentyl, cyclopentyl, isopentyl, 2-pentyl, 3-pentyl, tert-pentyl, hexyl, cyclohexyl, heptyl, octyl, nonyl, decyl, undecyl, dodecyl, tetradecyl, hexadecyl, octadecyl, and eicosyl; unsaturated hydrocarbon groups, typically alkenyl and alkynyl groups such as vinyl, allyl, propenyl, 1-methylpropenyl, butenyl, pentenyl, hexenyl, heptenyl, octenyl, nonenyl, decenyl, undecenyl, and octadecenyl; and aromatic hydrocarbon groups, typically aryl and aralkyl groups such as phenyl, naphthyl, anthryl, phenanthryl, pyrenyl, benzyl, phenethyl, phenylpropyl, 2-methylphenyl, 3-methylphenyl, 4-methylphenyl, 2,4-dimethylphenyl, 3,5-dimethylphenyl, 3,5-di-tert-butylphenyl, and biphenyl. Of these, preferred are methyl, ethyl, propyl, isopropyl, butyl, isobutyl, sec-butyl, tert-butyl, pentyl, hexyl, heptyl, octyl, nonyl, decyl, undecyl, dodecyl, vinyl, allyl and phenyl. Suitable alkoxy groups include methoxy, ethoxy, butoxy, tert-butoxy, and hexyloxy. Suitable aryloxy groups include phenoxy, p-methylphenoxy and naphthoxy. Suitable halogen atoms include fluorine, chlorine, bromine and iodine. Suitable amino groups include dimethylamino and diethylamino.

In formula (3), at least one of $R^{11}$ to $R^{20}$, especially $R^{11}$ and/or $R^{12}$ is a monovalent hydrocarbon group of 2 to 20 carbon atoms, especially 2 to 10 carbon atoms, which is terminated with an aliphatic carbon-carbon unsaturated bond and which may contain at least one —O—, —S— or —NR— or a combination thereof, with the proviso that two heteroatoms of oxygen, sulfur and nitrogen are not vicinal except for the cyclic monovalent hydrocarbon group. R is a monovalent hydrocarbon group of 1 to 20 carbon atoms, especially 1 to 12 carbon atoms. Where a plurality of R's are included in the substituent group, they may be the same or different and as exemplified above.

Suitable monovalent hydrocarbon groups terminated with an unsaturated bond include unsaturated hydrocarbon groups such as vinyl, isopropenyl, allyl, 1-methylpropenyl, 3-butenyl, 4-pentenyl, 5-hexenyl, 6-heptenyl, 7-octenyl, 8-nonenyl, 9-decenyl, 10-undecenyl, 11-dodecenyl, 12-tridecenyl, 13-tetradecenyl, 14-pentadecenyl, 15-hexadecenyl, 16-heptadecenyl, 17-octadecenyl, 18-nonadecenyl, 19-eicosenyl, ethynyl, propargyl, 3-butynyl, 4-pentynyl, 5-hexynyl, 6-heptynyl, 7-octynyl, 8-nonynyl, 9-decynyl, 10-undecynyl, and 11-dodecynyl; and heteroatom-containing hydrocarbon groups such as allyloxy, 2-oxa-4-pentenyl, 3-oxa-2-methyl-4-pentenyl, 3-oxa-5-hexenyl, 3-oxa-2-methyl-5-hexenyl, 3,6-dioxa-7-octenyl, 3-methyl-3-aza-4-pentenyl, 3-thia-4-pentenyl, 5-vinylfuran-2-yl, 5-vinylthiophen-2-yl, 5-vinyl-1,2,4-oxadiazol-3-yl, 5-vinyl-1,3,4-oxadiazol-2-yl, 5-vinyl-1,2,4-thiadiazol-3-yl, and Sx-H (4)

In formula (4), Sx is a straight, branched or cyclic organosiloxanyl group of 2 to 10 silicon atoms, preferably 3 to 10 silicon atoms, more preferably 5 to 10 silicon atoms, having a monovalent hydrocarbon group of 1 to 20 carbon atoms, especially 1 to 6 carbon atoms, bonded to a silicon atom. Examples of the monovalent hydrocarbon group are as exemplified above. The compound of formula (4) has a Si—H bond which is subject to hydrosilylation reaction.

Examples of the compound having formula (4) include linear organosiloxanes such as pentamethyldisiloxane, 3,3,3-triethyl-1,1-dimethyldisiloxane, pentaethyldisiloxane, 3-vinyl-1,1,3,3-tetramethyldisiloxane, 3-tert-butyl-1,1,3,3-tetramethyldisiloxane, 3,3,3-triisopropyl-1,1-dimethyldisiloxane, 1,1-diphenyl-3,3,3-trimethyldisiloxane, 3-methyl-1,1,3,3-tetraphenyldisiloxane, 1-cyclohexyl-1,3,3,3-tetramethyldisiloxane, heptamethyltrisiloxane, nonamethyltetrasiloxane, undecamethylpentasiloxane, tridecamethylhexasiloxane, pentadecamethylheptasiloxane, heptadecamethyloctasiloxane, nonadecamethylnonasiloxane, and heneicosamethyldecasiloxane; branched organosiloxanes such as 1-trimethylsiloxy-1,3,3,3-tetramethyldisiloxane, 1-trimethylsiloxy-1,3,3,5,5,5-hexamethyltrisiloxane, 1-pentamethyldisiloxanyloxy-1,3,3,5,5,5-hexamethyltrisiloxane, 1-trimethylsiloxy-1,3,3,5,5,7,7,7-octamethyltetrasiloxane, 1,1-bis(trimethylsiloxy)-3,3,3-trimethyldisiloxane; and cyclic organosiloxanes such as 1,3,3,5,5,7,7-heptamethylcyclotetrasiloxane and 1,3,5,7-tetramethyl-1,3,5,7-tetravinylcyclotetrasiloxane. Of these, preferred are pentamethyldisiloxane, heptamethyltrisiloxane, nonamethyltetrasiloxane, undecamethylpentasiloxane, 1-trimethylsiloxy-1,3,3,3-tetramethyldisiloxane, and 1,3,3,5,5,7,7-heptamethylcyclotetrasiloxane.

According to the invention, the fluorescent compound is prepared by reacting an olefin compound of formula (3) with an organosiloxane compound of formula (4) in the presence of a platinum catalyst. Suitable platinum catalysts used herein include platinum compounds such as chloroplatinic acid, platinum(0)-divinyltetramethyldisiloxane complex, platinum(0)-tetravinyltetramethylcyclotetrasiloxane complex, tetrakis(triphenylphosphine)platinum, dichlorobis(triphenylphosphine)platinum, dichlorobis(acetonitrile)platinum, dichlorobis(benzonitrile)platinum, and dichloro(cyclooctadiene)platinum; and platinum on solid supports such as platinum on active carbon and platinum on silica gel. Although the amount of the platinum catalyst used is not particularly limited, it is preferably used in an amount of 0.000001 to 0.01 mole, more preferably 0.00001 to 0.001 mole of platinum per mole of the olefin compound of formula (3).

Although the olefin compound of formula (3) may be combined with the organosiloxane compound of formula (4) in any mixing ratio, it is preferred for reactivity and productivity to use 0.5 to 2 moles, more preferably 1.0 to 1.2 moles of the compound of formula (4) per mole of the compound of formula (3).

Although the reaction temperature and time may be determined as appropriate by those skilled in the art, the temperature is preferably 0 to 200° C., more preferably 20 to 100° C. and the time is preferably 0.1 to 20 hours, more preferably 1 to 3 hours. The reaction may be performed in a solvent. Suitable solvents include ether, hydrocarbon and aprotic polar solvents, for example, pentane, hexane, diethyl ether, tetrahydrofuran, dioxane, toluene, xylene, acetonitrile, and N,N-dimethylformamide, which may be used alone or in admixture.

The foregoing reaction forms a compound having the general formula (1'), for example.

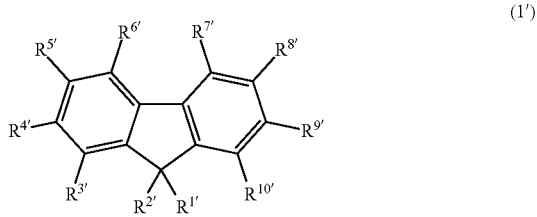

(1')

In formula (1'), $R^{1'}$ to $R^{10'}$ are each independently a substituent group selected from among a straight, branched or cyclic, monovalent hydrocarbon group of 1 to 20 carbon atoms, preferably 1 to 12 carbon atoms, alkoxy group of 1 to 20 carbon atoms, preferably 1 to 12 carbon atoms, aryloxy group of 6 to 20 carbon atoms, preferably 6 to 12 carbon atoms, halogen, hydrogen, amino, cyano and siloxane-containing group having the formula (2'), a pair of $R^{1'}$ and $R^{2'}$, $R^{3'}$ and $R^{4'}$, $R^{4'}$ and $R^{5'}$, $R^{5'}$ and $R^{6'}$, $R^{7'}$ and $R^{8'}$, $R^{8'}$ and $R^{9'}$, or $R^{9'}$ and $R^{10'}$ may bond together to form an alicyclic or aromatic ring structure of 5 to 8 carbon atoms with the carbon atom(s) to which they are attached. At least one of $R^{1'}$ to $R^{10'}$ is a siloxane-containing group having the formula (2').

Sx-A' (2')

In formula (2'), Sx is a straight, branched or cyclic organosiloxanyl group of 2 to 10 silicon atoms, preferably 3 to 10 silicon atoms, more preferably 5 to 10 silicon atoms, having a monovalent hydrocarbon group of 1 to 20 carbon atoms, preferably 1 to 6 carbon atoms bonded to a silicon atom, a silicon atom in Sx being bonded to A'. A' is a straight, branched or cyclic, divalent hydrocarbon group of 2 to 20 carbon atoms, preferably 2 to 12 carbon atoms which may contain at least one —O—, —S— or —NR— or a combination thereof, with the proviso that two heteroatoms of oxygen, sulfur and nitrogen are not vicinal except for the cyclic divalent hydrocarbon group. R is a monovalent $C_1$-$C_{20}$ hydrocarbon group.

Examples of $R^{1'}$ to $R^{10'}$ are the same as exemplified above for $R^1$ to $R^{10}$. Examples of A' are the same as exemplified above for A (excluding the groups of one carbon atom). Examples of formula (2') are the same as exemplified above for formula (2) (excluding the compounds wherein A has only one carbon atom).

It is noted that the compound having a siloxane-containing group of formula (2) wherein A is a single bond or a divalent hydrocarbon group of one carbon atom is prepared by reacting a halogen compound having the general formula (5) with a metal or organometallic compound to form a metalofluorene derivative and further reacting it with a silicon compound having the general formula (7).

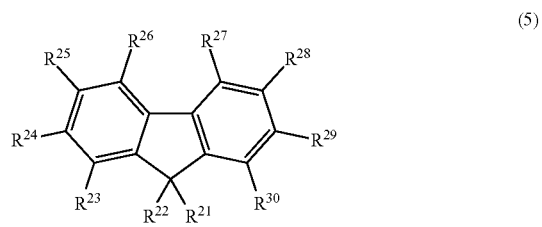

(5)

In formula (5), $R^{21}$ to $R^{30}$ are each independently a substituent group selected from among a straight, branched or cyclic, monovalent hydrocarbon group of 1 to 20 carbon atoms, especially 1 to 12 carbon atoms, alkoxy group of 1 to 20 carbon atoms, especially 1 to 12 carbon atoms, aryloxy group of 6 to 20 carbon atoms, especially 6 to 12 carbon atoms, halogen, hydrogen, amino, and cyano group.

In formula (5), at least one of $R^{21}$ to $R^{30}$, especially $R^{21}$ and/or $R^{22}$ contains a substituent group having the formula (6).

Hal-B- (6)

In formula (6), Hal is a halogen atom such as chlorine, bromine or iodine. B is a single bond or a divalent hydrocarbon group of one carbon atom which may contain —O—, —S— or —NR— or a combination thereof, with the proviso that two heteroatoms of oxygen, sulfur and nitrogen are not vicinal. R is a monovalent hydrocarbon group of 1 to 20 carbon atoms, preferably 1 to 12 carbon atoms. Where a plurality of R's are included in the substituent group, they may be the same or different. Examples of R are as exemplified above.

Examples of the group having formula (6) include chloromethyl, bromomethyl, iodomethyl, chloromethoxy, bromomethoxy, and iodomethoxy.

A pair of $R^{21}$ and $R^{22}$, $R^{23}$ and $R^{24}$, $R^{24}$ and $R^{25}$, $R^{25}$ and $R^{26}$, $R^{27}$ and $R^{28}$, $R^{28}$ and $R^{29}$, or $R^{29}$ and $R^{30}$ may bond together to form an alicyclic or aromatic ring structure of 5 to 8 carbon atoms with the carbon atom(s) to which they are attached.

Suitable monovalent hydrocarbon groups include saturated hydrocarbon groups, typically straight, branched or cyclic alkyl groups such as methyl, ethyl, propyl, isopropyl, butyl, isobutyl, sec-butyl, tert-butyl, pentyl, cyclopentyl, isopentyl, 2-pentyl, 3-pentyl, tert-pentyl, hexyl, cyclohexyl, heptyl, octyl, nonyl, decyl, undecyl, dodecyl, tetradecyl, hexadecyl, octadecyl, and eicosyl; unsaturated hydrocarbon groups, typically alkenyl and alkynyl groups such as vinyl, allyl, propenyl, 1-methylpropenyl, butenyl, pentenyl, hexenyl, heptenyl, octenyl, nonenyl, decenyl, undecenyl, and octadecenyl; and aromatic hydrocarbon groups, typically aryl and aralkyl groups such as phenyl, naphthyl, anthryl, phenanthryl, pyrenyl, benzyl, phenethyl, phenylpropyl, 2-methylphenyl, 3-methylphenyl, 4-methylphenyl, 2,4-dimethylphenyl, 3,5-dimethylphenyl, 3,5-di-tert-butylphenyl, and biphenyl. Of these, preferred are methyl, ethyl, propyl, isopropyl, butyl, isobutyl, sec-butyl, tert-butyl, pentyl, hexyl, heptyl, octyl, nonyl, decyl, undecyl, dodecyl, vinyl, allyl and phenyl. Suitable alkoxy groups include methoxy, ethoxy, butoxy, tert-butoxy, and hexyloxy. Suitable aryloxy groups include phenoxy, p-methylphenoxy and naphthoxy. Suitable halogen atoms include fluorine, chlorine, bromine and iodine. Suitable amino groups include dimethylamino and diethylamino.

Examples of the metal and organometallic compound include n-butyl lithium, sec-butyl lithium, t-butyl lithium, methyl lithium, phenyl lithium, metallic lithium, metallic magnesium, methylmagnesium chloride, and methylmagnesium bromide. Although the amount of the metal or organometallic compound used is not particularly limited, it is preferably used in an amount of 1 to 10 moles, more preferably 1 to 1.5 moles per mole of the compound of formula (5).

The reaction temperature is preferably 100° C. to −100° C., more preferably −30° C. to −80° C. The reaction time is preferably 30 minutes to 10 hours, more preferably 30 minutes to 1 hour. Suitable solvents include ether and hydrocarbon solvents, for example, diethyl ether, tetrahydrofuran, hexane and pentane, which may be used alone or in admixture.

The metalofluorene derivative thus obtained is then reacted with a silicon compound having the general formula (7), yielding a compound having formula (1).

$$Sx-Y \qquad (7)$$

In formula (7), Sx is a straight, branched or cyclic organosiloxanyl group of 2 to 10 silicon atoms, preferably 3 to 10 silicon atoms, more preferably 5 to 10 silicon atoms, having a monovalent hydrocarbon group of 1 to 20 carbon atoms, especially 1 to 6 carbon atoms, bonded to a silicon atom. Examples of the monovalent hydrocarbon group are as exemplified above. Y is a halogen atom or an organoxy group of 1 to 10 carbon atoms, examples of which include chlorine, bromine, iodine, methoxy, ethoxy, isopropoxy, and phenoxy.

Examples of the silicon compound having formula (7) include linear organosiloxanes such as chloropentamethyldisiloxane, methoxypentamethyldisiloxane, 3,3,3-triethyl-1-chloro-1,1-dimethyldisiloxane, 3-vinyl-1-chloro-1,1,3,3-tetramethyldisiloxane, 3-tert-butyl-1-chloro-1,1,3,3-tetramethyldisiloxane, 1-chloro-3,3,3-triisopropyl-1,1-dimethyldisiloxane, 1-chloro-1,1-diphenyl-3,3,3-trimethyldisiloxane, 1-chloro-3-methyl-1,1,3,3-tetraphenyldisiloxane, and 1-chloro-1-cyclohexyl-1,3,3,3-tetramethyldisiloxane;

branched organosiloxanes such as 1-chloro-1-trimethylsiloxy-1,3,3,3-tetramethyldisiloxane, 1-methoxy-1-trimethylsiloxy-1,3,3,3-tetramethyldisiloxane, 1-chloro-1-trimethylsiloxy-1,3,3,5,5,5-hexamethyltrisiloxane, 1-chloro-1-pentamethyldisiloxanyloxy-1,3,3,5,5,5-hexamethyltrisiloxane, and 1-chloro-1-trimethylsiloxy-1,3,3,5,5,7,7,7-octamethyltetrasiloxane; and cyclic organosiloxanes such as 1-chloro-1,3,3,5,5,7,7-heptamethylcyclotetrasiloxane, 1-methoxy-1,3,3,5,5,7,7-heptamethylcyclotetrasiloxane, and 1-chloro-1,3,5,7-tetramethyl-1,3,5,7-tetravinylcyclotetrasiloxane.

Of these, preferred are chloropentamethyldisiloxane, 1-chloro-1-trimethylsiloxy-1,3,3,3-tetramethyldisiloxane, and 1-chloro-1,3,3,5,5,7,7-heptamethylcyclotetrasiloxane.

Although the metalofluorene derivative may be combined with the compound of formula (7) in any mixing ratio, it is preferred for reactivity and productivity to use 0.5 to 2 moles, more preferably 1.0 to 1.2 moles of the compound of formula (7) per mole of the metalofluorene derivative.

Although the reaction temperature and time may be determined as appropriate by those skilled in the art, the temperature is preferably 0 to 200° C., more preferably 20 to 100° C. and the time is preferably 0.1 to 20 hours, more preferably 1 to 3 hours. The reaction may be performed in a solvent. Suitable solvents include ether, hydrocarbon and aprotic polar solvents, for example, pentane, hexane, diethyl ether, tetrahydrofuran, dioxane, toluene, xylene, acetonitrile, and N,N-dimethylformamide, which may be used alone or in admixture.

A further embodiment of the invention is a fluorescent resin composition comprising a resin and the fluorescent compound defined herein. Suitable resins serving as a matrix include thermoplastic and thermosetting resins such as polyethylene, polypropylene, polystyrene, cycloolefin polymers, polyacrylate, polyvinyl chloride, polycarbonate, polyesters, polyamides, polyimides, polyvinyl alcohol, silicone resins, ethylene-vinyl alcohol copolymerized resins, ethylene-vinyl acetate copolymerized resins, ABS resins, epoxy resins, phenolic resins, melamine resins, and polyurethane; and elastomers such as natural rubber, nitrile rubber, urethane rubber, EPDM, styrene-butadiene rubber, fluoro-rubber, and silicone rubber. Inter alia, silicone resins including silicone oil, silicone rubber, silicone resin and silicone gel are preferred. The fluorescent resin composition may have any state of liquid, solid, rubber or gel.

In the fluorescent resin composition, preferably the fluorescent compound is uniformly dispersed without agglomeration. The fluorescent resin composition may contain two or more fluorescent compounds including the inventive fluorescent compound.

In the fluorescent resin composition, the fluorescent compound is present in any desired amount, preferably 0.001 to 10% by weight, more preferably 0.01 to 5% by weight, and even more preferably 0.1 to 5% by weight. Preferably, the amount of the fluorescent compound is determined as long as it is compatible with the matrix resin. Though depending on the nature of the fluorescent compound and the nature of the matrix resin, too large an amount of the fluorescent compound may lead to a lowering of fluorescent intensity due to density quenching whereas too small an amount may lead to an insufficient fluorescent intensity.

Besides the resin, the fluorescent resin composition may contain additives. Suitable additives include solvents such as water, methanol, ethanol, hexane, isooctane, decane, toluene, xylene, dimethylformamide, dimethylacetamide, methylpyrrolidone, and dimethyl sulfoxide; fillers such as silica gel, titanium oxide, zinc oxide, carbon and magnesium hydroxide; silicon compounds such as silane coupling agents as well as tetramethoxysilane, tetraethoxysilane, hexamethyldisiloxane, and decamethylcyclopentasiloxane; radical polymerization initiators such as azobisisobutyronitrile and benzoyl peroxide; photo-polymerization initiators such as 2-hydroxy-1-methylpropiophenone and diphenyliodonium hexafluorophosphate; metal compounds such as chloroplatinic acid, platinum(0)-divinyltetramethyldisiloxane complex, and benzylidene-dichlorobis(tricyclohexylphosphine) ruthenium; fibers such as glass fibers and carbon fibers; UV absorbers and photo-stabilizers such as benzophenone derivatives and hindered amine compounds; plasticizers such as phthalates and adipates; and flame retardants such as phosphates. The additives may be added to the composition as long as the emission properties of the composition are not compromised. Typically the additives are added to the composition in amounts of 0.01 to 80% by weight.

The fluorescent compound may be combined with other components to form the fluorescent resin composition, for example, by milling the resin and the fluorescent compound until the compound is dispersed in the resin, by premixing the fluorescent compound with a liquid resin monomer or prepolymer, dissolving therein, and effecting addition polymerization or condensation polymerization, or by dissolving the fluorescent compound in resin varnish.

EXAMPLE

Examples of the invention are given below by way of illustration and not by way of limitation. In the following structural formulae, Me stands for methyl.

Example 1

Synthesis of 2,7-dibromo-9,9'-di-[3-(1-trimethylsiloxy-1,3,3,3-tetramethyldisiloxan-1-yl)propyl]fluorene (Compound #1)

A 100-ml three-necked flask equipped with a reflux condenser and stirrer was purged with nitrogen and charged with 845.0 mg (2.11 mmol) of 2,7-dibromo-9,9'-diallylfluorene, 15.2 mg of a 2 wt % xylene solution of platinum(0)-1,3-divinyl-1,1,3,3-tetramethyldisiloxane complex, and 5 ml of dry toluene. To the flask, 1.01 g (4.54 mmol) of 1,1,1,3,5,5,5-heptamethyltrisiloxane was added dropwise over 10 minutes. After the completion of dropwise addition, the reaction solution was stirred for 6 hours at room temperature. The solution was concentrated in vacuum. Water and toluene were added to the concentrate, followed by separatory operation to extract the organic layer. The resulting solution was dried over magnesium sulfate and concentrated under reduced pressure on a rotary evaporator, yielding 1.70 g of a pale yellow liquid.

On time-of-flight mass spectrometry (MALDI-TOFMS) analysis, the liquid was identified to be 2,7-dibromo-9,9'-di-[3-(1-trimethylsiloxy-1,3,3,3-tetramethyldisiloxan-1-yl)propyl]fluorene, designated Compound #1.

MALDI-TOFMS m/z: 846.2 (M⁺)

The structure of Compound #1 is represented by the following formula (8).

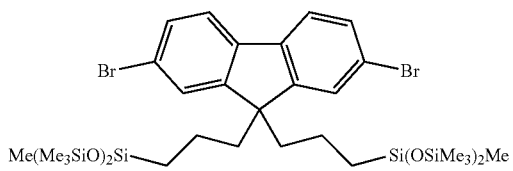

(8)

Example 2

Synthesis of 2,7-bis(biphenyl)-9,9'-di-[3-(1-trimethylsiloxy-1,3,3,3-tetramethyldisiloxan-1-yl)propyl]fluorene (Compound #2)

A 100-ml three-necked flask equipped with a reflux condenser and stirrer was purged with nitrogen and charged with 1.70 g (2.00 mmol) of 2,7-dibromo-9,9'-di[3-(1-trimethylsiloxy-1,3,3,3-tetramethyldisiloxan-1-yl)propyl]-fluorene, 1.02 g (5.15 mmol) of biphenylboronic acid, 131.4 mg (0.11 mmol) of tetrakisi(triphenylphosphine), and 20 ml of dimethoxyethane. To the flask, 1.10 g (7.96 mmol) of potassium carbonate in 4 ml of water was added dropwise. After the completion of dropwise addition, the reaction solution was stirred for 4.5 hours at 67° C. Water and toluene were added to the solution, followed by separatory operation to extract the organic layer. The resulting solution was dried over magnesium sulfate, concentrated under reduced pressure on a rotary evaporator, and purified by HPLC, yielding 1.48 g of a white solid.

On NMR and MALDI-TOFMS spectroscopy analysis, the solid was identified to be 2,7-bis(biphenyl)-9,9'-di-[3-(1-trimethylsiloxy-1,3,3,3-tetramethyldisiloxan-1-yl)propyl]-fluorene, designated Compound #2.

¹H-NMR (600 MHz, d in CDCl₃): −0.18 (s, 6H), −0.10 (s, 36H), 0.25-0.30 (m, 4H), 0.77-0.89 (m, 4H), 7.26 (t, 2H), 7.49 (t, 4H), 7.61-7.63 (m, 4H), 7.67-7.76 (m, 12H), 7.78-7.81 (m, 2H)

MALDI-TOFMS m/z: 994.6 (M⁺)

The structure of Compound #2 is represented by the following formula (9).

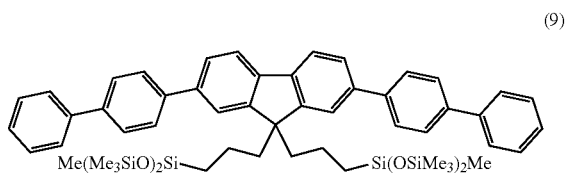

(9)

Compound #2 was also analyzed in ethanol by ultraviolet-visible absorption and fluorescent spectroscopy, finding a maximum absorption peak wavelength of 338 nm, a molar absorption coefficient of 7.07×10⁴, and a maximum fluorescence wavelength of 385 nm (excitation wavelength: 338 nm).

Example 3

Synthesis of 2,7-dibromo-9,9'-di-[3-(undecamethylpentasiloxan-1-yl)propyl]fluorene (Compound #3)

A 100-ml three-necked flask equipped with a reflux condenser and stirrer was purged with nitrogen and charged with 1.33 g (3.29 mmol) of 2,7-dibromo-9,9'-diallylfluorene, 15.0 mg of a 2 wt % xylene solution of platinum(0)-1,3-divinyl-1,1,3,3-tetramethyldisiloxane complex, and 6 ml of dry toluene. To the flask, 3.00 g (8.09 mmol) of 1,1,3,3,5,5,7,7,9,9,9-undecamethyltrisiloxane was added dropwise over 10 minutes. After the completion of dropwise addition, the reaction solution was stirred for 7 hours at room temperature. Water and toluene were added to the solution, followed by separatory operation to extract the organic layer. The resulting solution was dried over magnesium sulfate, concentrated under reduced pressure on a rotary evaporator, and purified by silica gel chromatography, yielding 2.63 g of a pale yellow liquid.

On MALDI-TOFMS analysis, the liquid was identified to be 2,7-dibromo-9,9'-di-[3-(undecamethylpentasiloxan-1-yl)-propyl]fluorene, designated Compound #3.

MALDI-TOFMS m/z: 1142.2 (M⁺)

The structure of Compound #3 is represented by the following formula (10).

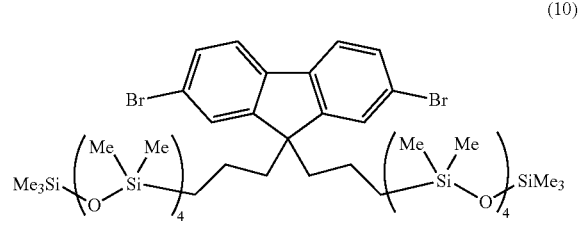

(10)

Example 4

Synthesis of 2,7-bis(biphenyl)-9,9'-di-[3-(undecamethylpentasiloxan-1-yl)propyl]fluorene (Compound #4)

A 100-ml three-necked flask equipped with a reflux condenser and stirrer was purged with nitrogen and charged with 2.02 g (1.76 mmol) of 2,7-dibromo-9,9'-di[3-(undecamethylpentasiloxan-1-yl)propyl]fluorene, 807.3 mg (4.08 mmol) of biphenylboronic acid, 98.0 mg (0.085 mmol) of tetrakisi(t-riphenylphosphine), and 13 ml of dimethoxyethane. To the flask, 848.0 mg (6.14 mmol) of potassium carbonate in 5 ml of water was added, followed by stirring for 7 hours at 84° C. Water and toluene were added to the solution, followed by separatory operation to extract the organic layer. The resulting solution was dried over magnesium sulfate, concentrated under reduced pressure on a rotary evaporator, and purified by HPLC, yielding 1.15 g of a colorless liquid.

On NMR and MALDI-TOFMS spectroscopy analysis, the liquid was identified to be 2,7-bis(biphenyl)-9,9'-di-[3-(undecamethylpentasiloxan-1-yl)propyl]fluorene, designated Compound #4.

$^1$H-NMR (600 MHz, d in CDCl$_3$): −0.12 (s, 12H), −0.10 (s, 12H), −0.012 (s, 12H), −0.010 (s, 12H), 0.070 (s, 18H), 0.35-0.40 (m, 4H), 0.80-0.86 (m, 4H), 2.08-2.14 (m, 4H), 7.36-7.40 (m, 2H), 7.46-7.51 (m, 4H), 7.60-7.65 (m, 4H), 7.66-7.69 (m, 4H), 7.69-7.78 (m, 8H), 7.78-7.81 (m, 2H)

MALDI-TOFMS m/z: 1290.5 (M$^+$)

The structure of Compound #4 is represented by the following formula (11).

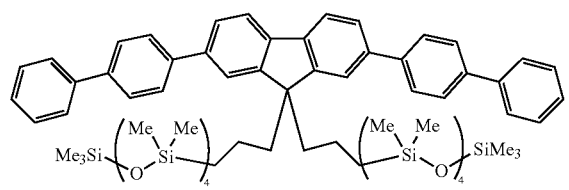

(11)

Compound #4 was also analyzed in ethanol by ultraviolet-visible absorption and fluorescent spectroscopy, finding a maximum absorption peak wavelength of 338 nm, a molar absorption coefficient of 6.81×10$^4$, and a maximum fluorescence wavelength of 383 nm (excitation wavelength: 338 nm).

Example 5

Silicone Resin Composition Containing Compound #2

In a glass vial, 114.2 mg of Compound #2 synthesized in Example 2 was weighed. With stirring at room temperature, transparent silicone resin SIM-360 matrix (Shin-Etsu Chemical Co., Ltd.) was added in incremental amounts. The compound was judged dissolved when the solution became transparent, from which a solubility of 1.3 mmol/L was computed. A curing agent was added to this mixture in an amount of 10% by weight based on the matrix. The mixture was deaerated and cured by heating at 150° C. for 30 minutes, yielding a fluorescent silicone resin composition. The concentration of Compound #2 could be altered to any arbitrary value below the indicated concentration.

Example 6

Silicone Resin Composition Containing Compound #4

As in Example 5, the solubility of Compound #4 in silicone resin SIM-360 matrix was measured, finding a solubility of 6.0 mmol/L. A curing agent was added to the mixture in an amount of 10% by weight based on the matrix. The mixture was deaerated and cured by heating at 150° C. for 30 minutes, yielding a fluorescent silicone resin composition. The concentration of Compound #4 could be altered to any arbitrary value below the indicated concentration.

Comparative Example 1

Solubility of 2,7-Bis(Biphenyl)-9,9'-Dihexylfluorene (Compound #5) in Silicone Resin Compound #5 has the structure of the following formula (12).

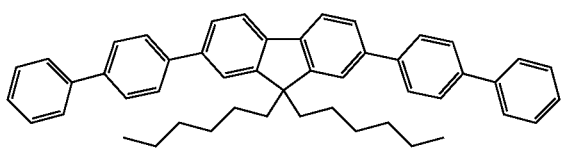

(12)

As in Example 5, the solubility of Compound #5 in silicone resin SIM-360 matrix was measured. The mixture became a suspension and the compound could not be dissolved.

The fluorescent compounds within the scope of the invention can be used as fluorescent ink, wavelength converting substance or the like. With the fluorescent compounds, low polar resins such as silicone resins can be colored without detracting from transparency, yielding highly transparent fluorescent resin compositions. Thus the invention is of great utility.

Japanese Patent Application No. 2012-027589 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:
1. A fluorescent compound having the general formula (1):

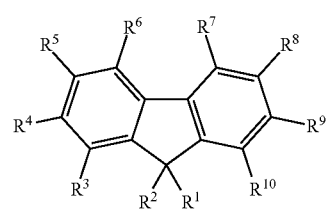

(1)

wherein
R$^1$ to R$^{10}$ are each independently a substituent group selected from the group consisting of a straight, branched or cyclic, monovalent C$_1$-C$_{20}$ hydrocarbon group, $C_1$-$C_{20}$ alkoxy group, $C_6$-$C_{20}$ aryloxy group, hydrogen, amino, cyano and siloxane-containing group having the formula (2), a pair of $R^1$ and $R^2$, $R^3$ and $R^4$, $R^4$ and $R^5$, $R^5$ and $R^6$, $R^7$ and $R^8$, $R^8$ and $R^9$, or $R^9$ and $R^{10}$ may bond together to form a ring structure of 5 to 8 carbon atoms with the carbon atoms to which they are attached, at least one of $R^1$ to $R^{10}$ is a siloxane-containing group having the formula (2), $$\text{Sx-A-} \tag{2}$$

wherein Sx is a straight, branched or cyclic organosiloxanyl group of 2 to 10 silicon atoms having a $C_1$-$C_{20}$ monovalent hydrocarbon group bonded to a silicon atom, a silicon atom in Sx being bonded to A, and A is a single bond or a straight, branched or cyclic, divalent $C_1$-$C_{20}$ hydrocarbon group which may contain at least one —O—, —S— or —NR— or a combination thereof, with the proviso that two heteroatoms of oxygen, sulfur and nitrogen are not vicinal except for the cyclic divalent hydrocarbon group, and R is a monovalent $C_1$-$C_{20}$ hydrocarbon group.

2. The fluorescent compound of claim 1 wherein the siloxane-containing group having formula (2) contains at least 5 silicon atoms in total.

3. The fluorescent compound of claim 1 wherein $R^1$ and/or $R^2$ in formula (1) is a siloxane-containing group having formula (2).

4. The fluorescent compound of claim 1 wherein $R^4$ and/or $R^9$ in formula (1) is biphenyl.

5. A fluorescent resin composition comprising the fluorescent compound of claim 1 and a resin.

6. The composition of claim 5 wherein the resin is a silicone resin.

7. A method for preparing a fluorescent compound having formula (1')

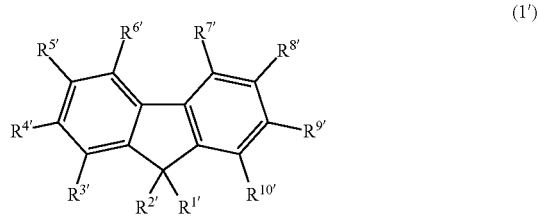

wherein
$R^{1'}$ to $R^{10'}$ are each independently a substituent group selected from the group consisting of a straight, branched or cyclic, monovalent $C_1$-$C_{20}$ hydrocarbon group, $C_1$-$C_{20}$ alkoxy group, $C_6$-$C_{20}$ aryloxy group, halogen, hydrogen, amino, cyano and siloxane-containing group having the formula (2'), a pair of $R^{1'}$ and $R^{2'}$, $R^{3'}$ and $R^{4'}$, $R^{4'}$ and $R^{5'}$, $R^{5'}$ and $R^{6'}$, $R^{7'}$ and $R^{8'}$, $R^{8'}$ and $R^{9'}$, or $R^{9'}$ and $R^{10'}$ may bond together to form a ring structure of 5 to 8 carbon atoms with the carbon atoms to which they are attached, at least one of $R^{1'}$ to $R^{10'}$ is a siloxane-containing group having the formula (2'), $$\text{Sx-A'-} \tag{2'}$$

wherein Sx is a straight, branched or cyclic organosiloxanyl group of 2 to 10 silicon atoms having a $C_1$-$C_{20}$ monovalent hydrocarbon group bonded to a silicon atom, a silicon atom in Sx being bonded to A', and A' is a straight, branched or cyclic, divalent $C_2$-$C_{20}$ hydrocarbon group which may contain at least one —O—, —S— or —NR— or a combination thereof, with the proviso that two heteroatoms of oxygen, sulfur and nitrogen are not vicinal except for the cyclic divalent hydrocarbon group, and R is a monovalent $C_1$-$C_{20}$ hydrocarbon group, said method comprising reacting an olefin compound having the formula (3)

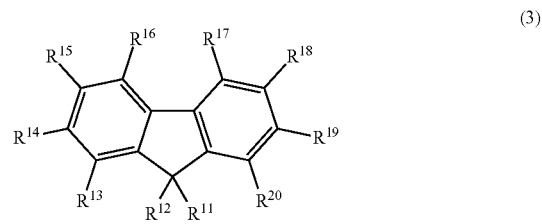

wherein $R^{11}$ to $R^{20}$ are each independently a substituent group selected from the group consisting of a straight, branched or cyclic, monovalent $C_1$-$C_{20}$ hydrocarbon group, $C_1$-$C_{20}$ alkoxy group, $C_6$-$C_{20}$ aryloxy group, hydrogen, amino, and cyano group, a pair of $R^{11}$ and $R^{12}$, $R^{13}$ and $R^{14}$, $R^{14}$ and $R^{15}$, $R^{15}$ and $R^{16}$, $R^{17}$ and $R^{18}$, $R^{18}$ and $R^{19}$, or $R^{19}$ and $R^{20}$ may bond together to form a ring structure of 5 to 8 carbon atoms with the carbon atoms to which they are attached, at least one of $R^{11}$ to $R^{20}$ is a monovalent $C_1$-$C_{20}$ hydrocarbon group which is terminated with an aliphatic carbon-carbon unsaturated bond and which may contain at least one —O—, —S— or —NR— or a combination thereof, with the proviso that two heteroatoms of oxygen, sulfur and nitrogen are not vicinal except for the cyclic monovalent hydrocarbon group, R is a monovalent $C_1$-$C_{20}$ hydrocarbon group, with a SiH-containing siloxane compound having the general formula (4)

$$\text{Sx-H} \tag{4}$$

wherein Sx is a straight, branched or cyclic organosiloxanyl group of 2 to 10 silicon atoms having a $C_1$-$C_{20}$ monovalent hydrocarbon group bonded to a silicon atom in the presence of a platinum catalyst.

8. The fluorescent compound of claim 1, having formula (9)

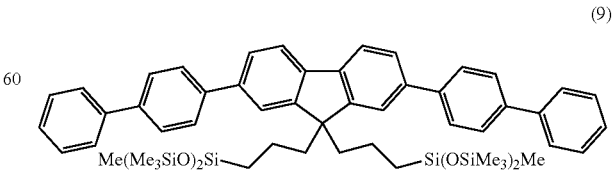

and the name 2,7-bis(biphenyl)-9,9'-di-[3-(1-trimethylsiloxy-1,3,3,3-tetramethyldisiloxan-1-yl)propyl]fluorine.

9. The fluorescent compound of claim 1, having formula (11)
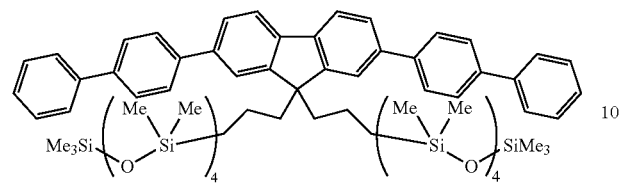
and the name 2,7-bis(biphenyl)-9,9'-di-[3-(undecamethyl-pentasiloxan-1-yl)propyl]fluorine.
* * * * *